US007402405B2

(12) United States Patent
Stallings

(10) Patent No.: US 7,402,405 B2
(45) Date of Patent: Jul. 22, 2008

(54) METHODS AND KITS FOR DIAGNOSING A PANCREATIC-BASED FAT MALABSORPTION DISORDER

(75) Inventor: Virginia A. Stallings, Geln Mills, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 345 days.

(21) Appl. No.: 10/162,837

(22) Filed: Jun. 5, 2002

(65) Prior Publication Data
US 2003/0086869 A1 May 8, 2003

Related U.S. Application Data

(60) Provisional application No. 60/295,916, filed on Jun. 5, 2001.

(51) Int. Cl.
*C12Q 1/34* (2006.01)
*G01N 33/92* (2006.01)
(52) U.S. Cl. .............................. 435/18; 436/71; 424/9.1
(58) Field of Classification Search .................... 435/19, 435/4, 975
See application file for complete search history.

(56) References Cited

U.S. PATENT DOCUMENTS

| 6,030,953 A | 2/2000 | Drapier et al. | |
|---|---|---|---|
| 2003/0086869 A1* | 5/2003 | Stallings ..................... | 424/9.1 |

OTHER PUBLICATIONS

Levy et al; Ameri. J. Physiol; vol. 262(2Pt 1), pp. G319-G326; (Feb. 1992) (Abstract Only).*
Goldstein et al. The Fatty Meal Test: An Alternative to Stool Fat Analysis; American Journal of Clinical Nutrition, vol. 38, Issue 5. (1983) pp. 763-768.*
Jonas et al. Oral Fat Loading Test: A Reliable Procedure for the Study of Fat Malabsorption in Children; Arch. Dis. Child, vol. 54 (1979) pp. 770-772.*
USDA Nutrient Database, Newer Knowledge of Dairy Foods; 2000. ☐☐From Wong et al, Fundamentals of Dairy Chemistry, 3rd Ed. 1988.☐☐http:www.nationaldairycouncil.org/nationaldairycouncil/nutrition/products/Table18.pdf.*
Adlung et al. On a New Method for Diagnosing Maldigestion Examinations With H3 Palmitic Acid/C14 Tripalmitate in Normal Persons and in Patients With Chronic Pancreatitis; Schweiz. Med. Wschr. vol. 105, No. 5 (1975) pp. 134-140. (English Translation).*
Dahiya et al. Comparative Study of Fatty Acid Composition in Human and Monkey Aorta; J. Biosci., vol. 6, No. 1 (1984) pp. 97-105.*
Kalivianakis et al. Detection of Impaired Intestinal Absorption of Long-Chain Fatty Acids: Validation Studies of a Novel Test in a Rat Model of Fat Malabsorption; Am. J. Clin. Nutr., vol. 72 (2000) pp. 174-180.*
Ahmed F et al, "Excessive faecal losses of vitamin A (retinol) in cystic fibrosis", Archives of Disease in Childhood 1990;65:589-593.

Amarri S et al, "13 Carbon mixed triglyceride breath test and pancreatic enzyme supplementation in cystic fibrosis", Arch Dis Child, 1997;76(4):349-351.
Benini L et al, "Near infrared spectrometry for faecal fat measurement: comparison with conventional gravimetric and titrimetric methods", Gut 1989;30:1344-1347.
Drummey GD et al, "Microscopical examination of the stool for steatorrhea", Medical Intelligence 1961;264(2):85-87.
Emmanuel B et al, "On the origin of rumen protozoan fatty acids", Biochimica et Biophysica Acta 1974;337:404-413.
Fitzsimmons SC et al, "The changing epidemiology of cystic fibrosis", Pediatrics 1993;122:1-9.
Goff JS, "Two-Stage Triolein Breath Test Differentiates Pancreatic Insufficiency from Other Causes of malabsorption", *Gastroenterology* 1982;83:44-46.
Green PHR et al, "Apolipoprotein localization and quantitation in the human intestine", Gastroenterology 1982;83:1223-1230.
Holmes GKT et al, "do we still need to measure faecal fat", British Medical Journal 1988;296(6636):1552-1553.
Jeejeebhoy KN et al, "Determination of fecal fats containing both medium and long chain triglycerides and fatty acids", Clin Biochem 1970;3:157-163.
Lloyd-Still JD et al, "The Effect of Intestinal Permeability on Pancreatic Enzyme-Induced Enteropathy in the Rat", J of Pediatric Gastroenterology and Nutrition 1998;26:489-495.
Newcomer AD et al, "Triolein Breath Tess: A Sensitive and Specific test for Fat Malabsorption", Gastroenterology 1979;76(1):6-13.
Pedersen NT et al, "The [14C]-triolein breath test is not valid as a test of fat absorption", Scand J Clin Lab Invest 1991;51:699-703.
Pencharz PB, "Nutritional Management of Cystic Fibrosis", Annu. Rev. Nutr. 1993;13:111-136.
Phuappradit P et al, "The steatocrit: a simple method for estimating stool fat content in newborn infants", Arch Dis Child. Sep. 1981;56(9):725-7.
Rader DJ et al, "Rapid in vivo transport and catabolism of human apolipoprotein A-IV-1 and slower catabolism of the Apoa-IV-2 isoprotein", The J of Clinical Investigation 1993;92:1009-1017.
Rigtrup KM et al, "Retinyl ester hydrolytic activity associated with human intestinal brush border membranes", Am J Clin Nutr 1994;60:111-116.
Rodriguez MD, "Rapid synthesis and secretion of intestinal apolipoprotein A-IV after gastric fat loading in rats", Am J Physiol Apr. 1997;272(4 Pt 2):R1170-1177.
Smyth RL et al, "Fibrosing colonopathy in cystic fibrosis: results of a case-control study", The Lancet 1995;346(8985):1247-1251.
Tran M et al, "The acid steatocrit: A much improved method", J of Pediatric Gastroenterology and Nutrition 1994;19:299-303.
Van De Kamer JH et al, "Malabsorption syndrome", Proceedings of the Fifth International Congress on Nutrition 1960, published by Federation of American Societies for Experimental Biology, p. 335-344.

(Continued)

*Primary Examiner*—Jon P Weber
*Assistant Examiner*—Paul C. Martin
(74) *Attorney, Agent, or Firm*—Dann, Dorfman, Herrell, & Skillman; Robert C. Netter, Jr.; Kathleen D. Rigaut

(57) ABSTRACT

The present invention relates to methods and kits useful in the diagnosis of a pancreatic-based fat malabsorption disorder in a mammal.

15 Claims, 24 Drawing Sheets

OTHER PUBLICATIONS

Watkins JB et al, "Diagnosis and Differentiation of Fat Malabsorption in Children using 13C-Labeled Lipids: Trioctanoin, Triolein, and Palmitic Acid Breath Test", Gastroenterology 1982;82:911-7.

N. Thorsgaard Pedersen: "Fat Digestion Tests", Digestion 37: suppl. 1, pp. 25-34 (1987).

N. thorsgaard Pedersen et al, "Simultaneous Assessment of Fat Maldigestion and Fat malabsorptio by a Double-isotope Method Using Fecal Radioactivity", Gastroenterology 88:47-54 (1985).

Hatakeyama K et al., "Differential Diagnosis of Maldigestion and Malasorptio of Fat", Japanese Journal of Surgery vol. 11, No. 4, pp. 263-271, 1981.

Hubbard V. S. et al., "Absorption of Safflower Oil and Structured Lipid Preparations in patients with Cystic Fibrosis", Lipids, vol. 22, No. 6, pp. 424-428 (1987).

Farrell P.M. et al., "Fatty Acid Abnormalities in Cystic Fibrosis", Pediatric Research, vol. 19, No. 1, pp. 104-109 (1985).

Behrman, R.E., et al., eds., "Nelson Textbook of Pediatrics," W.B. Saunders Co., Philadelphia, PA, 16th ed., pp. 142-143, (2000).

Jones, P.J.H., et al., "Lipids, sterols, and other metabolites," pp. 92-98 in "Modern Nutrition in Health and Disease" 10th ed., David B. Troy, et al., eds., Lippincott Williams & Wilkins, Philadelphia, PA, (2006).

Lichtenstein, A.H., et al., "Lipids: absorption and transport," pp. 111-117 in "Present Knowledge in Nutrition" vol. 1, 9th ed., Barbara A. Bowman, et al., eds. International Life Sciences Institute, Washington DC (2006).

Sugita, A., et al. "Concentration of higher fatty acid in blood of a patient with inflammatory bowel disease," "Serum long chain fatty acids in the patients with inflammatory bowel disease," J. Japanese Soc. Gastroenterol., 82(1):65-71, (1985), 2 sheets of abstracts provided.

Hamanaka, Y. et al. "New diagnostic method for fat indigestion and malabsorption and its clinical usefulness," JJPEN, 14(1):3-8, (1992). 1 sheet of abstract provided.

Kawaguchi, A. "Studies on the characteristics of serum lipoproteins and the capacity for lipid absorption in eisai hyperbilirubinuria rat (EHBR)," Publication of Gifu University School of Medicine, 47(3/4):143-157, (1999). 2 sheets of abstracts provided.

* cited by examiner

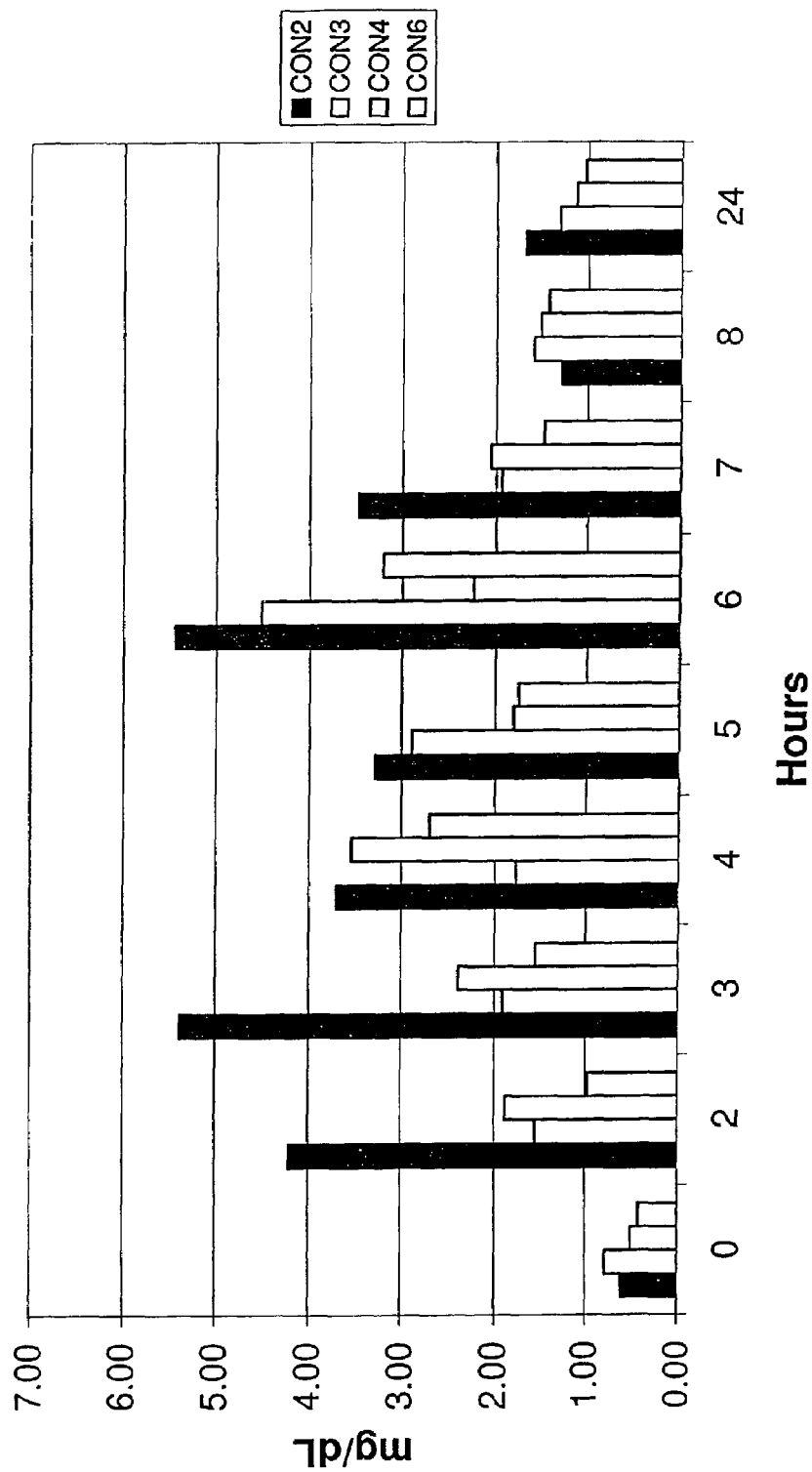

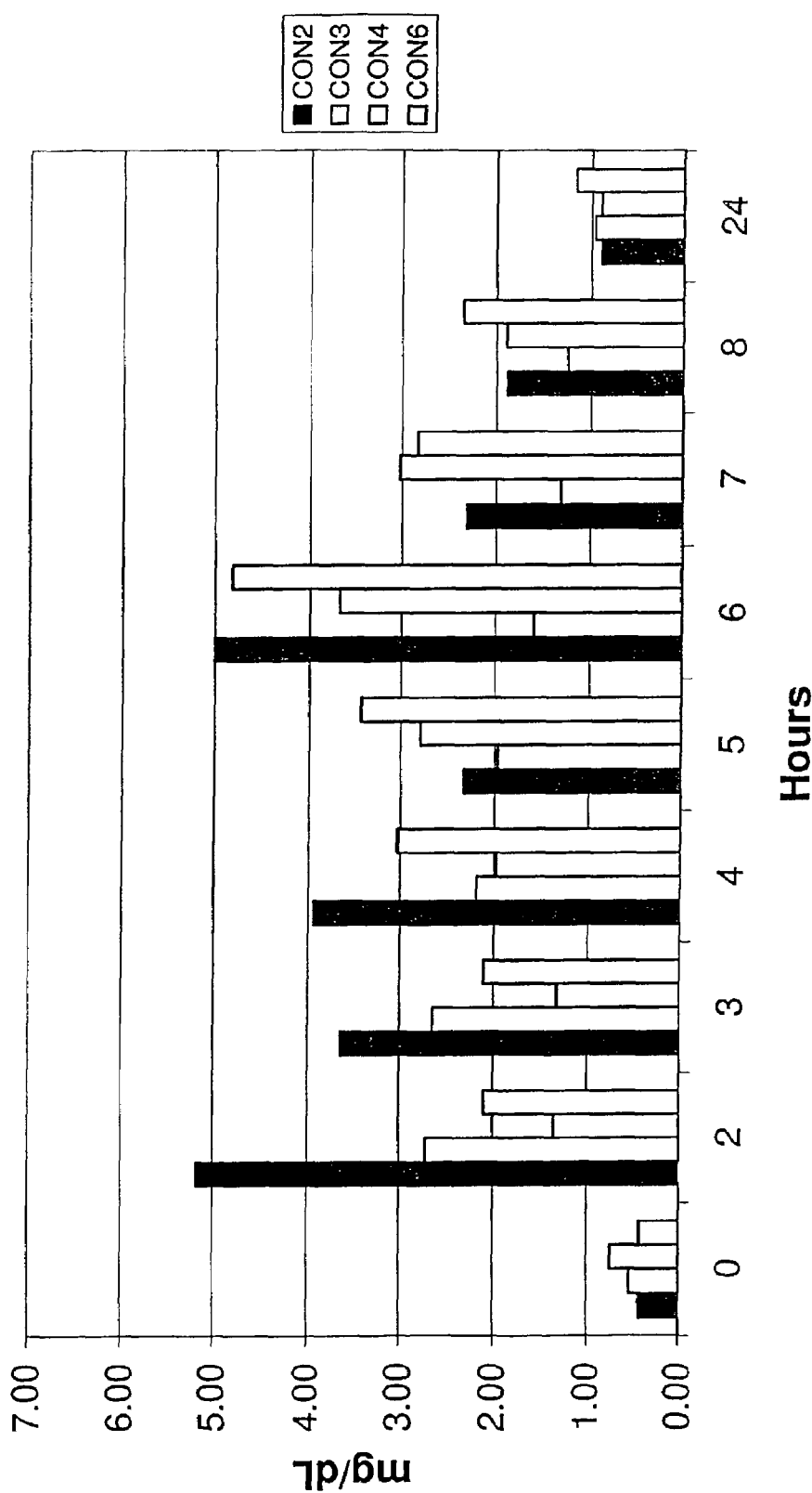

Figure 7

METHODS AND KITS FOR DIAGNOSING A PANCREATIC-BASED FAT MALABSORPTION DISORDER

This application claims priority to U.S. Provisional Application 60/295,916 filed Jun. 5, 2001, the entire disclosure of which is incorporated by reference herein.

FIELD OF THE INVENTION

This invention relates to improved methods for the diagnosis and assessment of fat malabsorption disorders.

BACKGROUND OF THE INVENTION

Cystic Fibrosis (CF) is the most common life-shortening autosomal recessive condition in the Caucasian population, with an estimated 25,000 people affected and seven million carriers in the U.S. alone.

Over the last 29 years, the median age of survival of people having CF has increased dramatically from 14 years in 1969 to 31 years of age in 1997. CF is therefore now both a pediatric and adult disease. Growth and nutritional status in people having CF are related to the severity of lung disease, the severity of pancreatic insufficiency, and to nutrient intake and absorption.

Considering national data (CFF Patient Registry), nutrition-related growth failure is still at an unacceptably high rate. In 1997, 19% of patients having CF were below the 5th percentile for height, and 24% were below the 5th percentile for weight. If the 10th percentile for weight is considered the more appropriate screen for patients with a nutritionally high-risk condition such as CF, then 33% of the patients with CF were below the desirable level in 1997. Except in the end stage of the lung disease, most of this growth failure and poor nutritional status (reduced weight for height) is associated with pancreatic insufficiency.

Improved treatment of pancreatic insufficiency in CF patients, as well as in other patients suffering from non-CF related malabsorption, requires an efficient clinical care test for malabsorption of nutrients through the intestinal wall. New pancreatic enzyme products or modifications of current products require evaluation in a research quality test for malabsorption. Given the occurrence of the previously unrecognized diagnosis of fibrosing colonopathy, accurate documentation of the severity of malabsorption is even more important to the CF care community and to patients having CF and pancreatic insufficiency (Smyth R. L., et al., 1995; Lancet, 346(8985):1247-51; Lloyd-Still, J. D., et al., 1998; J. Pediatr Gastroenterol Nutr., 26(5):489-95).

The important link between pancreatic insufficiency and malnutrition in children with CF was established over 40 years ago (Pencharz, P. B. et al., 1993; Annu. Rev. Nutr. 13:111-36). These investigators demonstrated that pancreatic enzymes improved fat absorption and led to positive nitrogen balance in the patient. Steatorrhea and malabsorption are the presenting symptoms in more than 20% of infants and children with CF. More than 85% of individuals with CF have pancreatic insufficiency and require exogenously added pancreatic enzymes in their diet (FitzSimmons, S. C., 1993; J. Pediatr., 122:1-9). Assessing the degree of fat malabsorption in the intestine is helpful for guiding both enzyme therapy and nutritional intervention in children and adults having CF and pancreatic insufficiency.

The are a variety of other pathological conditions that are associated with aberrant fat absorption. These include, without limitation, hereditary pancreatitis, α1 anti-trypsin deficiency, Shwachman Syndrome, Johanson-Blizzard Syndrome, sideroblastic anemia, pancreatic insufficiency, lipase deficiency, co-lipase deficiency in children, both partial and complete pancreatic surgical resection, pancreatic cancer, chronic and autoimmune pancreatitis, hyperlipidemia, and hyperparathyroidism. Improved methods for assessing aberrant pancreatic-based fat malabsorption in each of these disorders should facilitate diagnosis and the development of disease management regimens.

The 72-hour stool and diet collection method is considered the standard test for measuring the degree of fat malabsorption in a patient (Van De Kamer, J. H. et al., 1949; J. Biol Chem. 177:345-55; Jeejeebhoy, K. N. et al., 1970; Clin. Biochem. 3:157-63). A coefficient of fat absorption (CFA) obtained from the 72-hour stool collection and dietary intake method is widely accepted as a clinical, diagnostic, but non-specific, test for assessing fat malabsorption. The accuracy of this test is dependent on at least three days of entire stool collections together with consumption and documentation of a defined moderate to high fat diet. Despite its chemical accuracy, this test is prone to errors due to inadequate documentation of dietary intake, incomplete stool collections and day-to-day variation in fecal fat excretion (Holmes, G. K. T., 1988; BMJ, 296:1552). The technical and aesthetic difficulties associated with stool collection, storage and analysis make this test very unappealing to patients, families and lab workers. Few local laboratories conduct quantitative fecal fat analyses, thereby requiring additional time and expense for stools to be shipped to regional labs. The lag period between sample collection and reported results further fuels the disinterest in this test. Therefore, despite the clinically important data provided by the 72-hour stool and dietary collection method, this test is under-utilized or avoided in most clinical care and research settings. Even with the availability of capable labs, this potentially important clinical test is poorly accepted and under-utilized by both patients and care providers (Holmes, G. K. T., 1988; BMJ, 296:1552) thus contributing to the malnutrition and growth failure associated with CF.

Several alternative tests have been developed for assessing fat malabsorption, but all have significant limitations and have failed to gain wide acceptance as accurate or practical alternatives to the 72-hour stool and diet collection method. Several of these tests are discussed below.

The Spot Sudan III stain test is a qualitative test which involves the microscopic examination of a random fecal specimen stained with the Sudan dye (Drummey, G. D., et al., 1961; N. Engl. J. Med., 264:85-7). Even when objective criteria are used, the results are poorly reproducible in the ranges of mild to moderate steatorrhea common in patients with CF. The accuracy of this test is increased when homogenized pooled stool samples are used. However, from the patient's and family's perspective, this renders the test no different from the 72-hour stool collection method.

The Acid Steatocrit test utilizes a small (about 5 grams) stool specimen which is spun to separate the acidified fat from the solid stool (Tran, M., et al., 1994; J. Pediatr. Gastroenterol Nutr., 19:299-303; Phuapradit P., et al., 1981; Arch. Dis. Child., 56:725-7). Correlation with the 72-hour stool and diet collection method only occurs when homogenized-pooled stool is used. Therefore, requirement for a pooled stool collection offers no added benefit to the patient and family, and is not well correlated with the 72-hour collection method.

Breath tests, such as $^{14}C$ and $^{13}C$ Triolein breath tests (Newcomer, A. D., et al., 1979; Gastroenterology, 76:6-13; Watkins, J. B., et al., 1982; Gastroenterology, 82:911-7), are non-invasive tests utilizing small amounts of dietary fat labeled with stable or radioactive isotopes. Fat malabsorption is predicted by the labeled $CO_2$, and is an indicator of the absorbed dietary fat. The data may be used to qualitatively monitor response to pancreatic enzyme therapy in cases of known pancreatic insufficiency (Amarri, S., et al., 1997; Arch. Dis. Child., 76:349-51; Goff, J. S., 1982; Gastroenterology, 83:44-46). When compared with 72-hour stool and diet collection method, breath tests had up to 80% sensitivity but only 45% specificity (Pedersen, N. T., et al., 1991; Scand. J. Clin. Lab. Invest. 51:699-703). In using the breath test, there is also the assumption that the subject's pulmonary status is normal or near normal, which is not always the case in patients having CF. Also, $^{14}C$ is a radioactive compound, and therefore not suitable for use in children. $^{13}C$, the stable isotope, is safe for use in children, however, costs of the substrate and equipment required for analysis (mass spectrometry) are very high.

Retinyl palmitate, a long chain fat which is hydrolyzed by lipase prior to intestinal absorption via the chylomicron route, has successfully been used as marker for monitoring postprandial chylomicron response to dietary fat. However, the specificity of retinyl palmitate for assessing fat malabsorption due to pancreatic insufficiency in humans is limited because there are intrinsic gut brush border lipase enzymes which specifically hydrolyze retinyl esters (Rigtrup, K. M., et al., 1994; Am. J. Clin. Nutr., 60:111-116). In addition, specific defects involving the intestinal handling of retinol may occur in CF and other pancreatic-fat based malabsorption disorders, further limiting the use of this assay to monitor dietary fat malabsorption caused by pancreatic insufficiency (Ahmed, F., et al., 1990; Arch. Dis. Child., 65(6):589-593).

Apolipoprotein A-IV (A-4) is a 46-kD lipoprotein exclusively synthesized with chylomicrons in the enterocyte in response to dietary fat in humans (Green, P. H. R., et al., 1982; Gastroenterology, 83:1223-30). The rate of synthesis and secretion of this compound correlates with the consumption of dietary long chain triglycerides in a dose dependent pattern (Rodriguez, M-D., et al., 1997; Am. J. Physiol., 272:R1170-177). Since A-4 is rapidly catabolized, serum levels of this compound are dependent on rate of synthesis of A-4, and therefore A-4 may be used as a marker of absorbed dietary fat (Rader, D. J., et al., 1993; J. Clin. Invest., 92:1009-17). However, the immunoassays used for the detection of A-4 are not well standardized, thereby limiting broad, clinical utility.

The Pentadecanoic Acid (IPPA) test is a non-invasive qualitative test in adults used to evaluate pancreatic lipase activity. The assay involves oral administration of a radiolabeled triglyceride containing iodophenylpentadecanoic acid, $^{123}I$-IPPA, as a long chain fatty acid linked to position-3 of the glycerol backbone. Hydrolysis of the triglyceride by pancreatic lipase is required before IPPA is absorbed. After absorption, IPPA is metabolized by β-oxidation and the final metabolic product, $^{123}I$-p-iodobenzoic acid, is excreted in urine. Scintigraphic analysis of urine for $^{123}I$-p-iodobenzoic acid provides qualitative data about the activity of pancreatic lipase. However, the involvement of radioactivity limits broad applicability of this test to children.

Other tests which analyze stool for fat and energy content have been developed, including fecal bomb calorimetry and near infrared fecal spectroscopy (Benini, L., et al., 1989; Gut., 30:1344-7; Emmanuel, B., 1974; Biochem. Biophys. Acta., 337:404-13). In all cases, correlation with the 72-hour stool and diet collection method only occurs when pooled homogenized fecal samples are used. Therefore, these tests provide no added benefit to the patient and family than those described above.

All of the prior art assays have failed to become widely accepted in CF research or clinical care of patients with pancreatic fat-based malabsorption disorders. Thus, there remains a need in the art for improvements in methods for the diagnosis and nutritional care of patients with CF and other pancreatic insufficiency-related pathologies.

BRIEF SUMMARY OF THE INVENTION

In accordance with the present invention, diagnostic methods and kits are provided for diagnosing a pancreatic-based fat malabsorption disorder in a mammal, preferably a human. The method entails obtaining a baseline blood sample from the mammal followed by administration of a digestible composition comprising first and second fatty acid containing substrates, the first substrate being absorbable in the small intestine in the absence of pancreatic lipase hydrolysis thereof, and the second fatty acid requiring pancreatic lipase hydrolysis for absorption from the small intestine. Subsequent blood samples are then obtained to obtain absorption rates of the first and second fatty acid-containing substrates thereby generating a first absorption profile. This profile is then compared to a second absorption profile from a comparable control mammal, the control mammal being either positive or negative for a pancreatic-fat based malabsorption disorder. If the first absorption profile is similar to a second absorption profile obtained from a positive control animal having a pancreatic-based fat malabsorption disorder, a pancreatic-based fat malabsoption disorder is indicated in the first mammal. If the first absorption profile is similar to a second absorption profile obtained from a negative control animal which does not have a pancreatic-based fat malabsorption disorder, a pancreatic-based fat malabsorption disorder is not present in the first mammal.

Exemplary pancreatic-based fat malabsorption disorders which may be diagnosed using the method of the invention include without limitation, cystic fibrosis, hereditary pancreatitis, α1 anti-trypsin deficiency, Shwachman Syndrome, Johanson-Blizzard Syndrome, sideroblastic anemia, pancreatic insufficiency, lipase deficiency, co-lipase deficiency in children, both partial and complete pancreatic surgical resection, pancreatic cancer, chronic and autoimmune pancreatitis, hyperlipidemia, and hyperparathyroidism.

In another embodiment of the invention, a pancreatic-based fat malabsorption disorder is pharmaceutically induced in the second mammal. An exemplary agent for pharmaceutical induction of such a disorder is orlistat.

The foregoing summary, as well as the following detailed description of the invention, will be better understood when read in conjunction with the appended drawings.

BRIEF DESCRIPTION OF THE DRAWINGS

FIG. 3A shows PA levels in four healthy control subjects taking 30 mg/kg PA and 60 mg/kg THA over a 24 hour period.

FIG. 6 is a graph showing PA levels in four healthy control subjects taking 30 mg/kg PA and 90 mg/kg THA over a 24 hour time period.

FIG. 7 is a graph showing HA levels in four healthy control subjects taking 30 mg/kg PA and 90 mg/kg THA.

DETAILED DESCRIPTION OF THE INVENTION

Figure 1:
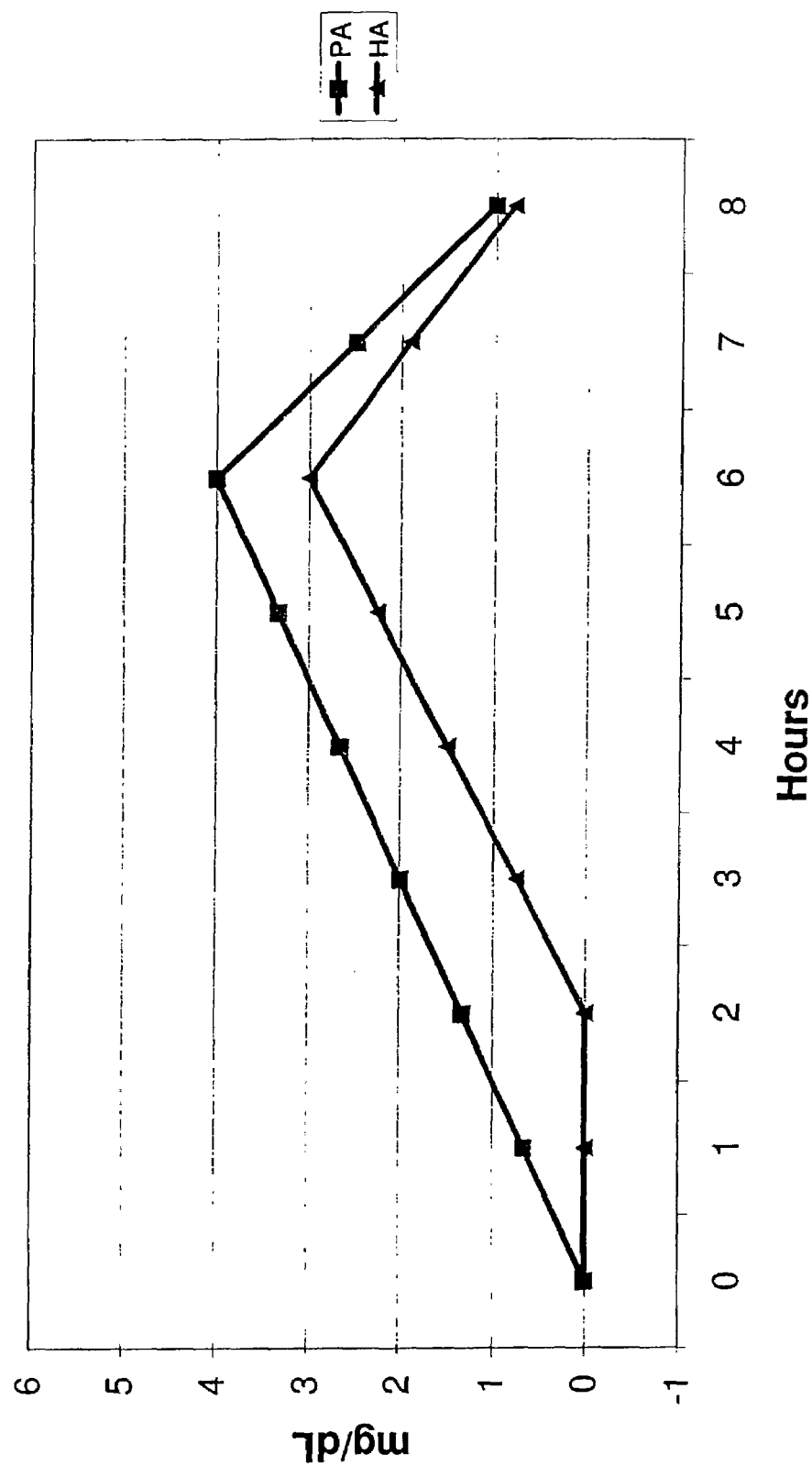
FIG. 1 is a graph showing a theoretical model for absorption of PA and HA over time in healthy controls. After administration of pentadecanoic acid (PA) and triheptadecanoin (THA), the absorption patterns of PA which does not require pancreatic lipase for adsorption and heptadecanoic acid (HA) which is absorbed after hydrolysis of THA by pancreateic lipase, are expected to differ in healthy individuals.

The present invention relates to methods and kits for accurate, reliable and specific measurement of pancreatic-based fat malabsorption and disorders thereof in a mammal. The inventive methods present more acceptable alternative tests to the 72-hour stool and diet collection method currently used as the standard method for measuring fat malabsorption due to pancreatic insufficiency in people having CF, but is broadly applicable to the diagnosis of other pancreatic-based fat malabsorption disease states, including, but without limitation, hereditary pancreatitis, α1 anti-trypsin deficiency, Shwachman Syndrome, Johanson-Blizzard Syndrome, sideroblastic anemia, pancreatic insufficiency, lipase deficiency, co-lipase deficiency in children, both partial and complete pancreatic surgical resection, pancreatic cancer, chronic and autoimmune pancreatitis, hyperlipidemia, and hyperparathyroidism.

The inventive method comprises a blood test which utilizes two naturally occurring saturated long chain fatty acids as substrates in a digestible composition which are used as markers of dietary fat absorption. After oral administration of the digestible composition, the difference in serum response patterns of the fatty acids resulting from hydrolysis by pancreatic lipase of the substrates are used to diagnose pancreatic-based fat malabsorption and disorders thereof. Mathematical or statistical modeling techniques can be used to develop a coefficient of fat absorption, which can be used to diagnose a pancreatic-based fat malabsorption disorder in a mammal.

Definitions

As used herein, each of the following terms has the meaning associated with it in this section. The articles "a" and "an" are used herein to refer to one or to more than one (i.e., to at least one) of the grammatical object of the article. By way of example, "an element" means one element or more than one element.

As used herein, a "pancreatic-based fat malabsorption disorder" means a disorder, disease or condition in a mammal in which malabsorption of one or more dietary fats is a symptom, wherein the disorder, disease or condition results from a deficiency in the function and/or the amount of a pancreatic lipase and/or colipase deficiency in the mammal. Fat malabsorption may also result from abnormal bile salt synthesis, excretion, deconjugation, reabsorption, impaired triglyceride resynthesis, chylomicron formation and/or excretion, or obstruction of intestinal lymphatics (Schmitz, J., Malabsorption, in *Pediatric Gastrointestinal Disease: Pathophysiology, Diagnosis and Management*, Walker, W. A., et al., eds. B. C. Decker Inc. Philadelphia, Pa., 1991, pgs. 79-89).

Disorders which may be assessed in accordance with the methods of the present invention, include, but without limitation, cystic fibrosis, hereditary pancreatitis, α1 anti-trypsin deficiency, Shwachman Syndrome, Johanson-Blizzard Syndrome, sideroblastic anemia, pancreatic insufficiency, lipase deficiency, co-lipase deficiency in children, both partial and complete pancreatic surgical resection, pancreatic cancer, chronic and autoimmune pancreatitis, hyperlipidemia, and hyperparathyroidism.

As used herein, a "digestible composition" means a composition which is digested by a mammal during normal digestive processes.

As used herein, the term "digestion" as used in the context of a "digestible composition" means acid hydrolysis and then lipase hydrolysis and/or proteolysis of a digestible composition in the stomach and small intestine of a mammal, respectively.

Description

The present invention includes a method of diagnosing a pancreatic-based fat malabsorption disorder in a mammal suspected of having such a disorder. The method comprises administering orally to the mammal a digestible composition comprising a first substrate, which can be absorbed from the small intestine of the mammal in the absence of pancreatic lipase hydrolysis thereof, and a second substrate, which cannot be absorbed from the small intestine of the mammal in the absence of pancreatic lipase hydrolysis thereof. The method also comprises permitting a sufficient period of time for digestion in the mammal of the digestible composition and absorption in the small intestine of the mammal of the first and second substrates. A baseline sample of blood is obtained from the mammal prior to orally administering the digestible composition, and one or more subsequent samples of blood are obtained from the mammal at one or more times following administration of the digestible composition.

The method then comprises assaying the levels of the fatty acids in the baseline sample and in one or more of the subsequent samples, which result from pancreatic lipase hydrolysis of and small intestinal absorption of the substrates. The method includes determining from the aforementioned levels of fatty acids, the rates of absorption from the small intestine of each of the aforementioned fatty acids in the mammal. The pattern of the rates of absorption is compared with the pattern of the rates of absorption for the fatty acids in an otherwise identical second mammal which is either afflicted with the pancreatic-based fat malabsorption disorder sought to be diagnosed, not afflicted with the pancreatic-based fat malabsorption disorder sought to be diagnosed, or in which the pancreatic-based fat malabsorption disorder sought to be diagnosed has been pharmaceutically induced. The otherwise identical second mammal serves as either the positive or negative control, whereby a pancreatic-based fat malabsorption disorder is diagnosed in the first mammal.

In the inventive method, the mammal can be any mammal, and is preferably a human. The pancreatic-based fat malabsorption disorder can be any pancreatic-based fat malabsorption disorder as described herein, and is preferably CF.

In a preferred embodiment, the pancreatic-based fat malabsorption disorder is the result of a deficiency in pancreatic lipase. The deficiency can be with regard to the amount and/or the function of pancreatic lipase in the mammal. However, as mentioned previously, aberrant pancreatic-based fat malabsorption can result from a variety of pathological conditions.

The digestible composition is administered orally by any method or regimen known to the skilled artisan for orally administering a substance, such as, for example, by administering the digestible composition in the form of a pill, a capsule, a tablet or a solid or liquid meal to be consumed by the mammal. The digestible composition of the invention may be administered in the form of an elixir. It may be also be mixed with frozen ice cream for example, to make it more palatable for the patient. An alternative means of administration comprises the insertion of an oral NG tube or a gastric tube directly into the stomach.

In a preferred embodiment, the digestible composition is orally administered to the mammal in the form of a meal, such as for example, a solid or liquid breakfast meal.

The digestible composition comprises a first and a second substrate which are, respectively, a fat which can be absorbed from the small intestine of the mammal in the absence of hydrolysis thereof by pancreatic lipase, and a fat which cannot be absorbed from the small intestine of the mammal in the absence of hydrolysis thereof by pancreatic lipase. The first substrate can be, by way of example and not by limitation, a saturated, long-chain free fatty acid, i.e., one having greater than 16 carbon atoms. Preferably, the first substrate is pentadecanoic acid (PA).

The second substrate can be, by way of example and not by limitation, a triglyceride comprising one or more saturated, long-chain fatty acids or a long chain fatty acid having an odd number of carbons, provided that the number of carbons exceeds 15. Any triglyceride composed or saturated or unsaturated long-chain fatty acids that requires pancreatic lipase for hydrolysis may be a potential candidate for the second substrate. Preferably, the second substrate is triheptadecanoin (THA).

PA is a 15-carbon saturated fatty acid (C15:0). THA is a triglyceride comprised of a glycerol backbone with three heptadecanoic (HA) saturated fatty acids each 17 carbons long (C17:0). Free fatty acids such as PA are absorbed from the small intestine of mammals without requiring hydrolysis by pancreatic lipase. However, triglycerides such as THA require hydrolysis by pancreatic lipase before HA can be released as a fatty acid and absorbed from the small intestine. Both PA and HA are naturally occurring saturated long-chain fatty acids having odd numbers of carbon atoms. Both are synthesized by bacteria, protozoa and ruminants (Emmanuel, B., 1974; Biochem. Biophys. Acta., 337:404-13). Humans cannot synthesize fatty acids having an uneven number of carbon atoms. The main dietary source of PA and HA in humans is dairy products, and the average daily dietary intake for PA and HA by humans ranges from about 150 to about 220 milligrams per day, respectively (Smith, L. M., 1961; J. Dairy Sci., 44:607-22; Barrefors, P., et al., 1995; J. Dairy Sci., 78:2691-9; Wolk, A., et al., Am. 1998; J. Clin. Nutr., 68:291-5; Smedman, A. E. M. et al., 1999; Am. J. Clin. Nutr., 69:22-9). Thus, patients to be assessed using the methods of the invention should restrict intake of dairy products prior to testing.

Triglyceride esters of both fatty acids (PA and HA) must be released by hydrolysis by pancreatic lipase before they can be absorbed from the small intestine as free fatty acids. Since both are long-chain fats, absorption into the blood is via the chylomicron lymphatic route, then to the blood. The metabolism of the resulting free fatty acids is via sequential beta oxidation to propionyl CoA, which is further metabolized to succinyl CoA at sites for β-oxidation in liver and myocardium (Champe, P. C., et al., 1994, Biochemistry, J. B. Lippincott Company, Philadelphia, Pa.; Schmitz B., et al., 1984; J. Lipid Res., 25:1102-8; Knapp, F. F., et al., 1993; J. Nucl. Med., 34:946-52). PA may be incorporated into adipose tissue and structural lipids, and therefore may be used as a marker for dairy fat intake (Wolk, A., et al., 1998; J. Clin. Nutr., 68:291-5; Smedman, A. E. M., et al., 1999; Am. J. Clin. Nutr., 69:22-9). Since serum concentrations of these fatty acids are very low and endogenous synthesis is absent in humans, PA and HA are ideal candidates for use as marker fats (Wolk, A., et al., 1998; Am. J. Clin. Nutr., 68:291-5).

The first substrate is present in the digestible composition in an amount ranging from about 10 to about 100 milligrams/kilogram body weight, and preferably is present in an amount from about 25 to 60 milligrams/kilogram body weight. Alternatively, a single dose unit of approximately 2 to 9 grams may be consumed. Most preferably, a single dose of 2.5 grams is given.

The second substrate is present in the digestible composition in an amount ranging from about 20 to about 200 milligrams/kilogram body weight, and preferably is present from about 60 to about 120 milligrams/kilogram body weight. Alternatively, a single dose unit of approximately 4 to 9 grams may be consumed. Most preferably, a single dose of 5 grams is given.

In an alternative embodiment, the two substrates are administered at equimolar doses, e.g., 5 grams of PA and 5.5 grams of THA.

Optionally, both the first and second substrates may be detectably labeled. Suitable detectable labels include without limitation any substance whose detection or measurement, either directly or indirectly, by physical or chemical means, is indicative of the presence of the substance to be assayed in the test sample. Representative examples of useful detectable labels, include, but are not limited to the following: molecules or ions directly or indirectly detectable based on light absorbance, fluorescence, reflectance, light scatter, phosphorescence, or luminescence properties; molecules or ions detectable by their radioactive properties; molecules or ions detectable by their nuclear magnetic resonance or paramagnetic properties. Included among the group of molecules indirectly detectable based on light absorbance or fluorescence, for example, are various enzymes which cause appropriate substrates to convert, e.g., from non-light absorbing to light absorbing molecules, or from non-fluorescent to fluorescent molecules. While radioactive detectable labels may be utilized in the methods of the invention, they are the least preferred, particularly in circumstances where children are being assessed for a pancreatic-based fat malabsorbtion disorder.

The inventive method also comprises permitting a sufficient period of time for ingestion in the mammal of the digestible composition, and absorption from the small intestine of the mammal of the substrates. The period of time may range from about 0 to about 24 hours, and is preferably from about 0 to about 8 hours.

The method of the invention also comprises obtaining a baseline sample of blood from the mammal prior to orally administering the digestible composition, and obtaining one or more subsequent samples of blood from the mammal at one or more times following administration of the digestible composition. The subsequent samples of blood obtained from the mammal may be obtained during a time period from about 5 minutes to about 24 hours following administration of the digestible composition, and are preferably obtained from about 10 minutes to about 8 hours after administration of the digestible composition. The minimum number of samples to be taken after administration of the digestible composition is 1. However, it is preferred that 4-5 samples be taken, preferably every hour after ingestion of the digestible composition.

The inventive method also comprises assaying the levels of the fatty acids in the baseline sample and in one or more of the subsequent samples which result from the absorption from the small intestine of the first substrate, and the hydrolysis by pancreatic lipase and absorption from the small intestine of the second substrate. The levels of the fatty acids in these samples can be assessed using any method known to the skilled artisan for quantitatively assessing the amount of a fatty acid in a blood or serum sample. Such methods include without limitation, mass spectroscopy.

In a preferred embodiment, the levels of the fatty acids in the sample are assessed using a quantitative gas-liquid chromatography method. Such techniques are known in the art and are described, for example, in Smith, L. M., 1961; J. Dairy Sci., 44:607-22, which describes the quantitative analysis of the fatty acid content of rumen milk using gas-liquid chromatography (GLC) with detection of all the major and minor fatty acids including PA and HA. Protozoa and bacteria present in the rumen of cattle produce odd carbon length long-chain saturated fatty acids such as PA and HA (Emmanuel, B., 1974; Biochem. Biophys Acta, 337:404-13). PA and HA have been reported to comprise less than 1% of serum lipids in humans (Smedman, A. E. M., et al., 1999; Am. J. Clin. Nutr., 69:22-9). Despite these low concentrations, both fatty acids have been successfully quantified in the serum using GLC and the levels have been found to correlate with dietary intake of dairy products. Wolk, A., et al. (1998; Am. J. Clin. Nutr., 68:291-5) quantified the human adipose tissue content of PA and HA in humans using GLC. The adipose tissue content of PA and HA has also been correlated to dietary intake of dairy products. Using weighed food records, the average daily intake of PA and HA has been estimated based upon GLC methods as 220 and 150 milligrams, respectively, in adults who consumed dairy products. PA and HA are thus commonly ingested as part of the dietary fat in people who consume any type of dairy products.

An example of a preferred GLC assay method is described hereinbelow.

The method of the invention also comprises determining, from the levels of fatty acids assessed in the samples as described above, the rates of absorption of each of the fatty acids derived from the first and second substrates from the small intestine in the mammal. The rates of absorption can be determined mathematically or statistically using any method known to the skilled artisan for calculating rates of absorption of lipids or pharmacological compounds from the small intestine into the lymphatic system or into the bloodstream. Examples of such calculations are described herein in the Examples.

In a preferred embodiment, one or more coefficients of fat absorption (CFAs) are calculated based upon the rates of absorption for each of the fatty acids resulting from the absorption and/or hydrolysis of the first and second substrates of the digestible composition. The calculation of a CFA is described herein in the Examples. Briefly, in the context of a serum sample, the amount of a fatty acid absorbed into the serum of a mammal at a given time point after administration of the digestible composition is calculated by subtracting out the amount of the same fatty acid present in the baseline serum sample from the amount of the fatty acid measured by assaying serum levels of the same fatty acid at the given time point. This amount of the fatty acid absorbed is expressed as a percentage of the fatty acid administered to the mammal in the digestible composition, and this percentage value is referred to as the CFA.

The inventive method also includes comparing the pattern of the rates of absorption obtained as described above with the pattern of the rates of absorption for the same fatty acids obtained from an otherwise identical second mammal after subjecting the mammal to the method described above. The comparison of the patterns of the rates of absorption can be accomplished using any mathematical or statistical method known to the skilled artisan. Typical mathematical and statistical methods useful for this purpose are provided herein.

As noted before, the otherwise identical second mammal is any mammal which can serve as either a positive or negative control in the diagnosis of a pancreatic-based fat malabsorption disorder.

In one preferred aspect, the otherwise identical second mammal is a mammal which is afflicted with the pancreatic-based fat malabsorption disorder sought to be diagnosed in the first mammal. In this aspect, the second mammal serves as the positive control, and if the pattern of the rates of absorption obtained as described above in the first mammal are found to be mathematically or statistically similar upon comparison to the pattern of the rates of absorption obtained as described above for the second mammal, the pancreatic-based fat malabsorption disorder sought to be diagnosed in the first mammal is present. Any mathematical or statistical method known to the skilled artisan can be used in the mathematical or statistical analysis.

In another preferred aspect, the otherwise identical second mammal is a mammal in which the pancreatic-based fat malabsorption disorder sought to be diagnosed is pharmaceutically induced. By way of example and not by limitation, a pancreatic lipase inhibitor compound can be used to induce a temporary condition of pancreatic insufficiency.

A preferred pharmaceutical compound for inhibiting pancreatic lipase is orlistat (XENICAL®, Roche Pharmaceuticals, Nutley, N.J.). A method of pharmaceutically inducing a pancreatic-based fat malabsorption disorder using orlistat is described herein in the Examples. In this aspect, the second mammal serves as a positive control. If the pattern of the rates of absorption obtained as described above in the first mammal are found to be mathematically or statistically similar upon comparison to the pattern of the rates of absorption obtained as described above for the second mammal, the pancreatic-based fat malabsorption disorder sought to be diagnosed in the first mammal is present. Any mathematical or statistical method known to the skilled artisan can be used in the mathematical or statistical analysis.

In yet another preferred aspect, the otherwise identical second mammal is a mammal which is not afflicted with the pancreatic-based fat malabsorption disorder sought to be diagnosed in the first mammal. In this aspect, the second mammal serves as a negative control. If the pattern of the rates of absorption obtained as described above in the first mammal are found to be mathematically or statistically similar upon comparison to the pattern of the rates of absorption obtained as described above for the second mammal, the pancreatic-based fat malabsorption disorder sought to be diagnosed in the first mammal is not present. As before, any mathematical or statistical method known to the skilled artisan can be used in the mathematical or statistical analysis.

Preferably, one or more CFAs calculated as described herein are used in diagnosing a pancreatic-based fat malabsorption disorder by comparing the patterns of the rates of absorption discussed above.

The present invention also includes a kit for diagnosing a pancreatic-based fat malabsorption disorder in a mammal. The kit comprises an instructional material useful for conveying the use of the inventive method in diagnosing a pancreatic-based fat malabsorption disorder in a mammal. As used herein, an "instructional material" includes a publication, a recording, a diagram, or any other medium of expression which can be used to communicate the usefulness of the inventive method for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

The kit also comprises a digestible composition comprising a first substrate which can be absorbed from the small intestine of the mammal in the absence of pancreatic lipase hydrolysis thereof and a second substrate which cannot be absorbed from the small intestine of the mammal in the absence of pancreatic lipase hydrolysis thereof. The digestible composition can be any of the digestible compositions described herein.

The kit further comprises a tube or a vial or the like for obtaining a sample of blood from said mammal.

METHODS AND PROTOCOLS TO FACILITATE THE PRACTICE OF THE PRESENT INVENTION

In accordance with the present invention, dietary intake is assessed using a weighed food record (St. Jeor, S. T., et al., 1983; J. Am. Diet Asso., 83:155-62). The record is used as the measure of dietary intake. Information about pancreatic enzymes, vitamin, mineral and other types of nutrient supplement consumption is recorded in the food intake records. The 'Nutritional Data System' (NDS) software developed by the University of Minnesota Nutrition Coordinating Center, School of Public Health (Minneapolis, Minn.), is used to analyze food intake and diet records. The NDS has menu driven prompts for complete descriptions of foods and preparation methods. This level of detail is required for research quality calculations of dietary intake for calories, protein, carbohydrates, fat and micronutrients and ratios (Daniels, L. A., 1984; Appl. Nutr., 38A:110-18; Feskanich, D., et al., 1989; Comput. Methods Programs Biomed., 30:47-57). The database contains over 16,000 food items and is continually updated to reflect changes in the marketplace. The percent missing data is zero for calories, protein, and fat. Most other major nutrients have similarly low rates of missing data. A customized version of this program currently is being used by the National Health and Nutrition Examination Survey (NHANES III). The NHANES III has dietary data on over 30,000 Americans, and is the next generation of nutritional reference data (Briefel, R. R., et al., 1995; Am. J. Clin. Nutr., 62(suppl):1072S-80S). In addition, the detail available in this computer analysis program provides a better description of high calorie, high fat foods which are often recommended for children with CF. Any similarly accurate dietary data analysis software program can be used.

Fecal Fat Analysis

The 72-hour stool collection coincides with the measurement of dietary intake. The stool is analyzed for total fat content by a gravimetric method for calculation of the coefficient of fat absorption using the method of Jeejeebhoy at the Mayo Medical Laboratories (Rochester, Minn.) (Jeejeebhoy, K. N., et al., 1970; Clin. Biochem, 3:157-63; Silverman, A., et al., 1983; Pediatric Clinical Gastroenterology, 901-2). The healthy adult patients in Example 1 are given a home collection kit (specimen can, collection container, gloves, scrapers) and detailed instructions. The specimens are stored frozen in the home and then shipped to the Mayo Laboratory for analysis. The patients with CF in Example 2 have the 72-hour stool collection conducted during their inpatient admission. Most families with children with CF have had previous experience with stool collection for fat analysis. The coefficient of fat absorption is calculated as follows:

$$\% \text{ Coefficient of fat absorption } (CFA) = \frac{\text{Fat intake (g)} - \text{Stool fat (g)}}{\text{Fat intake (g)}} \times 100$$

Anthropometric Assessment

The anthropometric measurement consists of weight, measured on a Scaletronix (White Plains, N.Y.) digital scale (to 0.1 kg); stature (to 0.1 cm), measured on a stadiometer (Crymych UK); skinfold thickness at the triceps, biceps, subscapular, and suprailiac for subcutaneous fat stores, measured with a Holtain (Crymych, UK) caliper; and circumference at the mid-upper arm measured with a non-stretchable plastic tape. Measurements follow the methods described in Lohman et al. (Lohman, T. G., et al., 1988; Anthropometric Standardization Reference Manual, Champaign, Ill.: Human Kinetcs Books). All measurements are taken and recorded in triplicate and the mean used in analysis.

GLC Analysis of Serum Samples

Both whole post-absorptive serum and isolated chylomicron fractions of the serum are analyzed for fatty acid composition. Chylomicrons are isolated from plasma by centrifugation at d=1.006 g/ml for 30 minutes at 26,000 g (Hatch, F. T., et al., 1968; Adv. Lipid Res., 6:1-68). Total lipids are extracted from each specimen following the method of Bligh and Dyer (Bligh, E. G., et al., 1959; Can. J. Biochem., 37:911-917). Following transmethylation of the lipid extracts using $BF_3$-methanol, fatty acid composition is determined using gas-liquid chromatographic (GLC) analysis using a Hewlett Packard GLC equipped with a flame ionization detector, an automatic 7673 sampler and 100 mm×0.25 mm ID column composed of a 0.20 micron film of SP-2560 (Supelco, Bellefonte, Pa.) (Morrison, W., et al., 1964; J. Lipid Res. 5:600-608). The temperature is programmed to change from 140° C. to 240° C. at a rate of 4° C./minute. At the time of extraction, heptadecanoic methyl ester is added as an internal standard.

Modeling

Analysis of the baseline and subsequent half-hourly or hourly serum samples taken for up to eight hours for the three doses of pentadecanoic acid (PA) and triglyceride containing heptadecanoic fatty acids (THA) are used to create time-dependent measured and normalized measured (see below) dosage response curves. Each concentration is analyzed independently for each subject and as a complete set for all subjects to determine the rates of absorption, distribution, and elimination for each of the measured fatty acids PA and heptadecanoic acid (HA) and the pancreatic enzyme activity for the hydrolysis of THA. The simplest model to determine a coefficient of fat absorption and an index of pancreatic enzyme activity is derived from the set of normal subjects and subsequently applied to subjects before and during therapy with a pancreatic enzyme inhibitor (orlistat). Finally, this model is applied to subjects with CF receiving various levels of enzyme therapy to determine their coefficient of fat absorption and their index of enzymatic activity.

Biological factors which are involved in determining the serum levels of the fatty acids PA and HA are: 1) the transit time through the gastrointestinal tract; 2) pancreatic enzyme activity to release HA from THA; 3) interaction with bile acids within the gastrointestinal tract; 4) absorption at the gastric mucosa interface into the chylomicron fraction; 5) distribution of the chylomicron fraction into its body compartments, including the plasma; and 6) elimination from the body.

The measurements of PA in the first set of normal subjects is used to determine the interplay of the absorption and elimination steps described above except for step 2 (the pancreatic enzyme activity), which is only involved in the absorption model for HA. Measured and normalized measured values of the whole plasma concentration and the chylomicron fraction concentration of PA are compared as independent test variables. A baseline measurement of PA (and HA) is subtracted from subsequent measurements so that only the PA (and HA) received from the dose of digestible composition is analyzed for the coefficient of absorption ($CFA_{MBT}$). The dose-related time dependent behavior for each of these data sets is compared, and the independent test variable exhibiting the simplest time dependent behavior is used for analysis. Any dose dependence of the test variable is also determined from this initial analysis, which is performed by plotting the data as a function of time and by calculating the mean and standard deviation for each of the measured and normalized measured data sets.

The measured plasma concentration is normalized using the initial dose divided by the test subject's plasma compartment volume, which is calculated from the test subject's BMI, as the denominator. The chylomicron fraction is normalized using the dose received divided by the chylomicron compartment volume as the denominator. The chylomicron volume is calculated from the fraction of the plasma volume extracted as chylomicrons multiplied by the total plasma volume determined for the test subject from the BMI, and using the plasma compartment estimated from the BMI as above. The dose of HA used in normalization is determined as the weight of HA delivered in the dose of THA.

In the simplest possible situation, the measured levels of both HA and PA are dose independent and reach an early and prolonged steady state in either whole plasma or in the chylomicron fraction. In that case, the normalized PA and HA can be compared against a CFA measured using the conventional standard 72 hour stool and diet collection method for the same patient and an appropriate conversion factor (which may be dependent upon the BMI) can be determined from the data. The ratio of the normalized HA to the normalized PA is defined as an index reflecting the pancreatic enzymatic activity profile during the absorption phase. The data is analyzed for any dependence of this index upon the patient's age or BMI. The comparisons before and after therapy with orlistat are expected to reflect a decrease in this index of approximately 70%.

If there is not a sufficiently prolonged steady state, more complexity is added to the analysis of the data. As stated above, the data for PA are analyzed first, since it does not involve pancreatic enzyme activity. It is assumed that the steps for absorption, distribution, and elimination of PA and HA are essentially the same and would have virtually the same rate constants and distribution fractions because of the similarity of these fatty acids. As such, PA is the simpler system because it excludes pancreatic enzyme activity. The index of the pancreatic enzyme activity is determined by analyzing the data for HA with a step for pancreatic enzyme activity superimposed upon the model and using the already determined constants for absorption, distribution, and elimination determined from the analysis of PA.

A two-phase model with systemic distribution into one compartment (either the plasma compartment or the chylomicron compartment) and rate limiting first order kinetics for absorption and elimination is used to model the normalized independent variables as a function of time. Additional complexity based upon exchange kinetics between the chylomicron and the plasma compartments, and if needed the introduction of an additional extravascular compartment, or of more complex kinetics of absorption or elimination, is compared to find the best model which explains the data. The underlying philosophy is that the degrees of freedom introduced in the model should approximate or be less than those of the measurements. Given that both the chylomicron and the plasma fractions are measured, the data can support a more complex model. Once the appropriate model and constant to describe the rate of absorption, distribution, and elimination are determined from the data for PA, an optimal time for the measurement of PA is estimated and used in subsequent data collections.

For THA, a simple model of catalysis is used to describe the kinetics of pancreatic enzyme activity, where PE represents the pancreatic enzyme and k1 and k2 are the rate constants for the forward and reverse reactions, respectively, of enzyme-substrate binding, and k3 is the rate constant for conversion of the bound enzyme-substrate complex to a final product and the release of the enzyme for further activity. The three doses of THA are used to determine whether either excess of substrate or a rate-limiting step can be applied as an assumption to simplify the model. In addition, testing during dosing with the pancreatic enzyme inhibitor orlistat is used to determine the complexity required to analyze the data over a range of enzyme activity. Analysis of these two data sets is used to determine an optimal time for measurement of HA. Comparison of the fraction of absorbed HA to the fraction of absorbed PA is used to index the pancreatic enzyme activity. The estimated activity in the presence of the orlistat is expected to be about 70% of the normal (unsuppressed) activity. Adjustments are made as needed and this model is applied to the randomized set of subjects with CF receiving varying doses of pancreatic enzymes to determine whether this method can be used to assess enzymatic activity and coefficient of fat absorption.

Statistical Analysis and Mathematical Modeling of Results

The Coefficient of Fat Absorption (CFA) obtained from MBT ($CFA_{MBT}$) along with the CFA obtained from the 72-hour stool and diet collection method ($CFA_{72}$) are the main outcomes in these experiments. Plots such as histograms and boxplots as well as summary descriptions such as means, medians, ranges, standard deviations and standard error of the means are examined.

To compare $CFA_{MBT}$ with $CFA_{72}$, the variability associated with each is examined by using the coefficient of variation (CV) to assess which of the two measures has less variability. The coefficient of variation (CV) is the standard deviation presented as a percentage of the mean.

The second step in the analysis is to examine the association between the $CFA_{MBT}$ and $CFA_{72}$. The data for all subjects are plotted using scatter plot and Pearson or Spearman correlation coefficients are obtained. It is expected that $CFA_{MBT}$ can explain at least 80% ($R^2$) of the variation in $CFA_{72}$.

In Example 3, to examine how $CFA_{MBT}$ responds to changes in pancreatic enzyme dose, subjects with CF and pancreatic insufficiency on routine doses of prescribed pancreatic enzymes are randomized to receive either 0% or 50% of their routine enzyme dose. Each group is analyzed separately at two specified reduced doses of the pancreatic enzymes and the change in $CFA_{MBT}$ is examined using the paired t-test if the distribution of $CFA_{MBT}$ is normal. If the distribution is not normal, a non parametric test, such as the Wilcoxon sum rank test, is used to analyze the data.

The invention is now described with reference to the following Examples. These Examples are provided for the purpose of illustration only and the invention should in no way be construed as being limited to these Examples, but rather should be construed to encompass any and all variations which become evident as a result of the teaching provided herein.

EXAMPLE 1

Pancreatic-Based Fat Malabsorption Studies Involving Healthy Adults

As mentioned previously, certain long-chain fatty acids require hydrolysis by pancreatic lipases prior to absorption. It is hypothesized that absorption rates of these fatty acids will differ from those which do not require hydrolysis. In order to test this hypothesis, PA, which does not require pancreatic lipase for absorption, and THA, which is hydrolyzed to heptadecanoic acid (HA) prior to absorption, were administered to healthy individuals as a test breakfast meal.

Subjects

Healthy control subjects between 18 and 50 years of age were selected. Exclusion criteria included: any chronic illness known to affect nutrient absorption, body mass index (BMI) <21 or >30 kg/m$^2$ (generally accepted healthy adult ranges), therapy with lipid lowering drugs, diabetes mellitus (NIDDM and IDDM), disorders associated with altered energy metabolism (e.g., hypothyroidism) and disinterest in participating in all three dosing experiments. This adult age range was selected for several reasons: (a) adult subjects are likely to remain committed to all three components of the study; (b) adults will understand the need to provide reliable feedback on taste and tolerance of the test breakfast meal and the entire malabsorption test procedure; and (c) adult subjects are able to plan the experimental day for full cooperation with the multiple phlebotomy events from 0700 to 1500 hours.

Protocol

Upon arrival at the study center, subjects had their weight and height measured and an experienced phlebotomist inserted a self-retaining intravenous catheter with a heparin lock for serial blood sampling. After initially drawing 2 milliliters of blood into a sterile syringe, the experimental blood sample (2 milliliters) was drawn and immediately stored in a 4-milliliter serum separator tube. Thereafter, the initial 2 milliliters of blood was infused back into the catheter followed by 2 milliliters of heparin flush. After the baseline blood samples were obtained, the subjects drank an approximately 8 to 12 ounce liquid test breakfast meal. This meal contained one to three doses of PA and THA in a random distribution. Subjects were asked to consume the test breakfast meal within five minutes. Thereafter, serial blood samples were obtained at regular intervals over a period ranging from 30 minutes to 24 hours. During the initial eight-hour period, subjects were permitted to ingest non-caloric and non-caffeinated beverages. A study protocol lunch of known fat content was provided and actual food intake was recorded. Ambulation was limited to maintain adherence to the 30 to 60 minute intervals in the blood sampling schedule. After completion of the blood sampling, the catheter was removed, a snack was offered, and the subjects were encouraged to consume a full meal. The lipid doses (mg/kg) of PA and THA used in this experiment were based on doses 10-fold higher than similar fats used to correct essential fatty acid deficiency in cystic fibrosis, and previous studies which used $^{13}$C radio-isotopes to qualitatively assess fat malabsorption in pancreatic disease (Rosenlund, M. L., et al., 1977;Pediatrics, 59:428-32; Wutzke, K. D., et al., 1999; J. Pediatr. Gastroenterol. Nutr., 29:148-54).

Results

A model of PA and HA absorption over time in healthy control subjects is presented in FIG. 1. Four healthy control subjects received 30 mg/kg PA and either 60 or 90 mg/kg THA at baseline. After administration of the fats in the digestible composition at baseline, serum levels of PA increased linearly over time as expected from negligible levels at baseline, reaching a peak at six hours of approximately 4 mg/dL, and declining thereafter to approximately 1 mg/dL by eight hours post dose. In contrast, serum levels of HA did not rise until after a minimum of two hours post-dose, giving sufficient time for the hydrolysis action of pancreatic enzymes to split the HA from its triglyceride (THA) precursor. After hydrolysis, serum levels of HA increased linearly over time, reaching a peak at 6 hours of approximately 3 mg/dL, and declined thereafter to approximately 1 mg/dL by eight hours post dose. Serum levels of PA and HA did not return to baseline by eight hours post dose. However, They were expected to fully return to baseline levels by 24 hours post dose.

Figure 2:
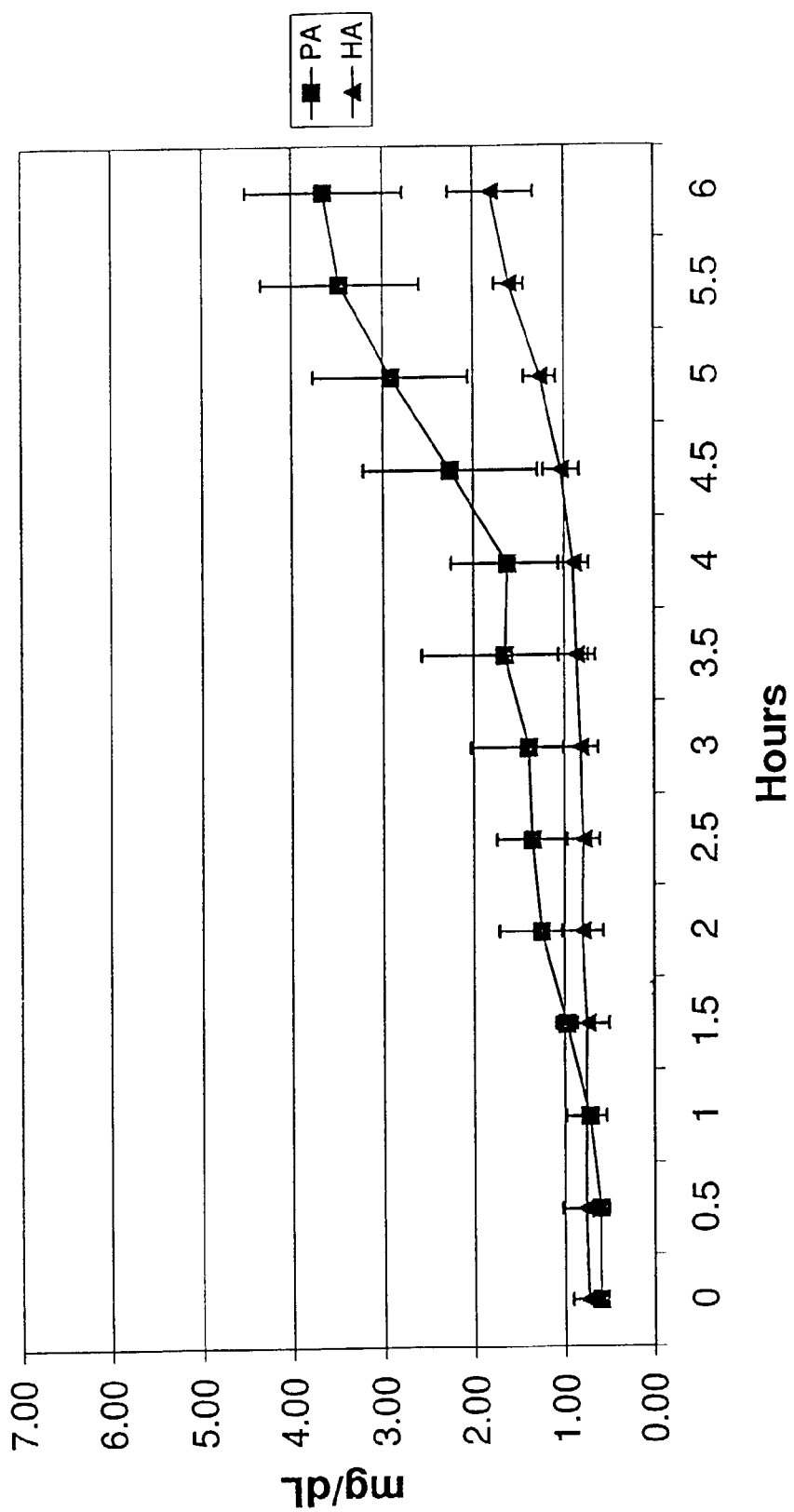
FIG. 2 is a graph depicting average fat absorption in four healthy control subjects taking 30 mg/kg PA and 30 mg/kg THA.

Four healthy control subjects were administered a dose of 30 mg/kg PA and 30 mg/kg THA in the digestible composition (a liquid breakfast shake) after a 12-hour fast. Blood was drawn at baseline before consumption of the shake and then every 30 minutes thereafter until hour 6. FIG. 2 shows the combined results for fat absorption by these four subjects. Following an approximately half hour delay, the PA rose nearly linearly over the measured time interval. For HA, there was a delay period of 3-4 hours, then a nearly linear increase in serum concentration. The preliminary data clearly demonstrated different patterns of absorption kinetics for PA and HA, where PA increased steadily over time after only a minor delay, where as HA increased only after a substantial delay of up to 4 hours.

It was determined from these initial results that: 1) a higher dose of THA would potentially yield more optimal information on the fat absorption pattern; 2) the number of blood draws could be reduced and the intervals between blood draws lengthened without losing valuable information regarding the absorption kinetics of the two fats; and 3) blood should be sampled over a longer period of time in order to capture the time at peak serum levels for the fats and the time required for the serum levels to return to baseline or near baseline.

After a 12 hour fast, four healthy control subjects were given 30 mg/kg PA and 60 mg/kg THA, and, more than one week later (to allow a washout period), the same four control subjects were given 30 mg/kg PA and 90 mg/kg THA in a digestible composition consisting of a liquid breakfast shake. Blood was sampled at baseline and then at hourly intervals from 2 to 8 hours and then sampled again at 24 hours. Subjects were fed a prepared lunchtime meal with a known quantity of fat (80 gms).

The individual results are presented for the four healthy control subjects taking 30 mg/kg PA and 60 mg/kg THA in FIG. 3A for PA. From very low serum levels at baseline, an increase in PA was evident by 2 hours with peak level reached at 6 hours, and a subsequent decline thereafter.

Figure 3B:
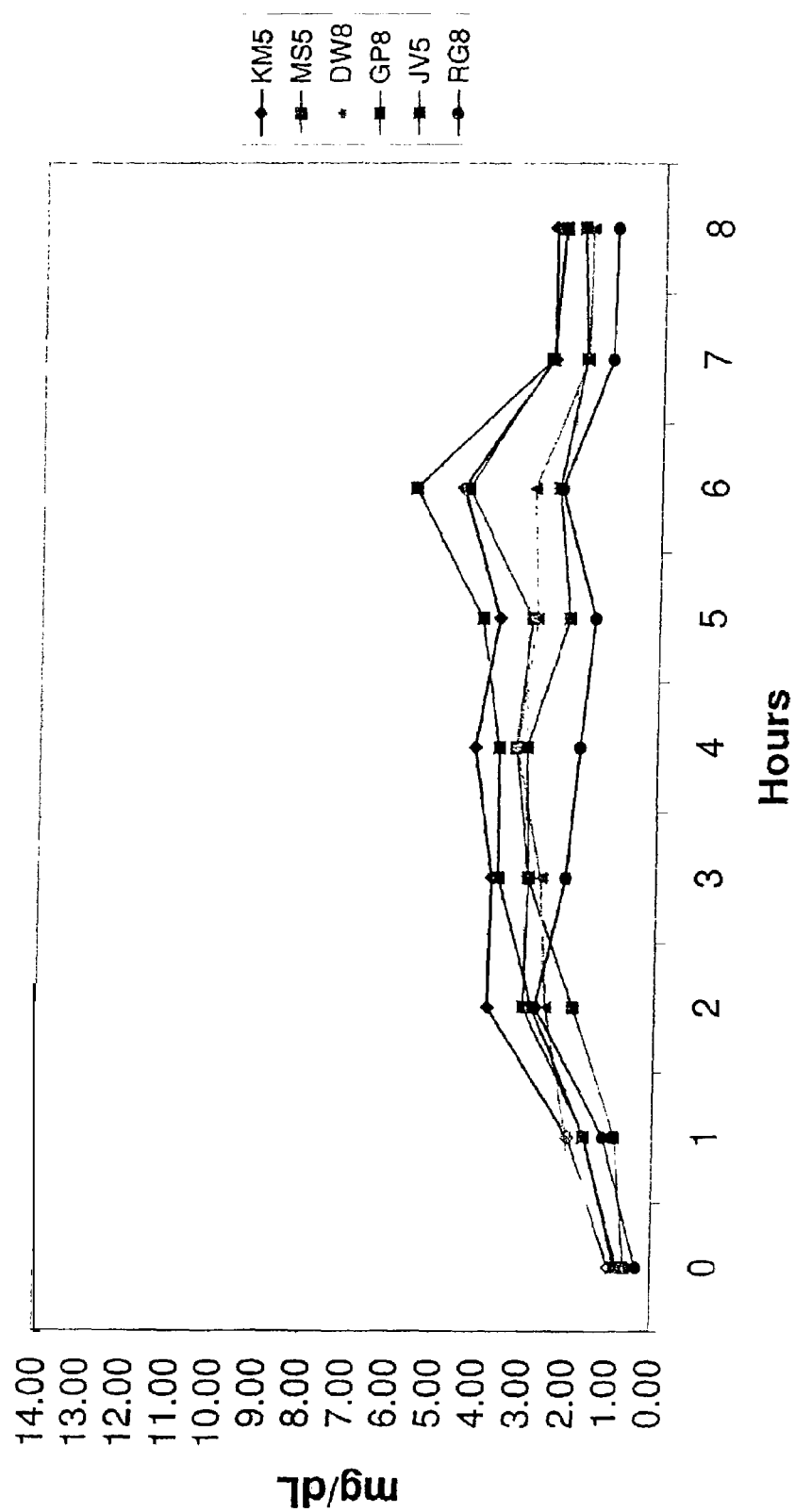
FIG. 3B is a graph showing the average of three tests on six healthy subjects taking a 2.5 gram dose of PA over an 8 hour period.

Additional experiments were performed to investigate the degree of inter- and intra-individual variability in serum response to the administration of PA and THA. Six healthy volunteers ages 18 to 50 received a dose of PA (2.5 grams) and THA (5.0 grams in three subjects and 8.0 grams in three subjects) in a test-retest protocol. FIG. 3B illustrates the average of three tests for each of the six individuals (4 women and 2 men) for PA. The results indicated that there was variability between individuals in serum response to PA (FIG. 3B). Despite the differences in response, the pattern of response between individuals was similar with PA increasing over the first two hours and remaining elevated through hour six.

Figure 3C:
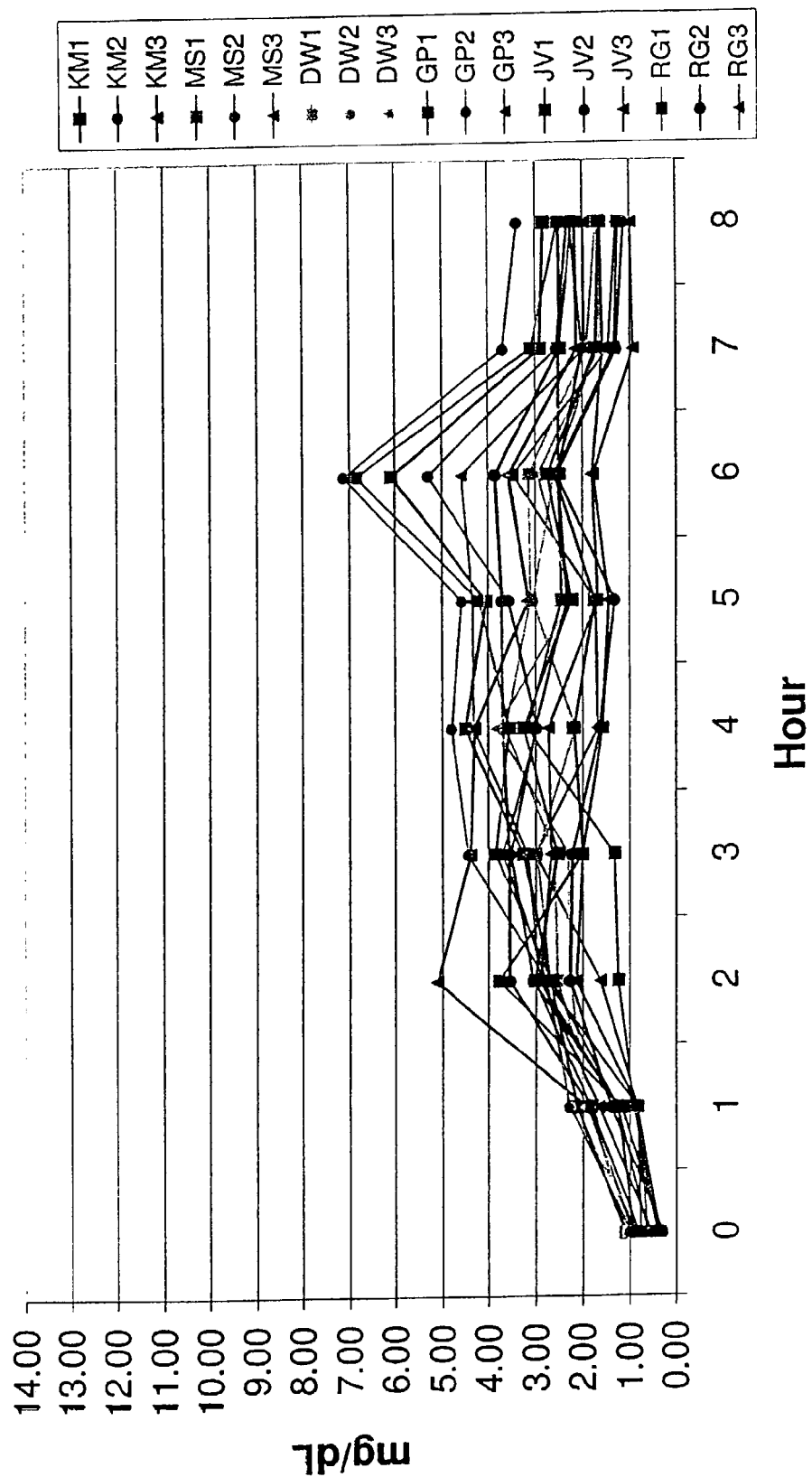
FIG. 3C is a graph showing all of the results from three separate tests on six healthy subjects taking 2.5 gram doses of PA. The average of these results is shown in FIG. 3B.

FIG. 3C shows all of the results of the three tests for all six individuals. There was less variability within individuals measured on separate occasions than there was between individuals. For example, the within-individual standard deviations ranged from 0.4 to 1.3 mg/dL for PA. In contrast, the between-individual standard deviations ranged from 0.6 to 1.3 mg/dL for PA.

Figure 4:
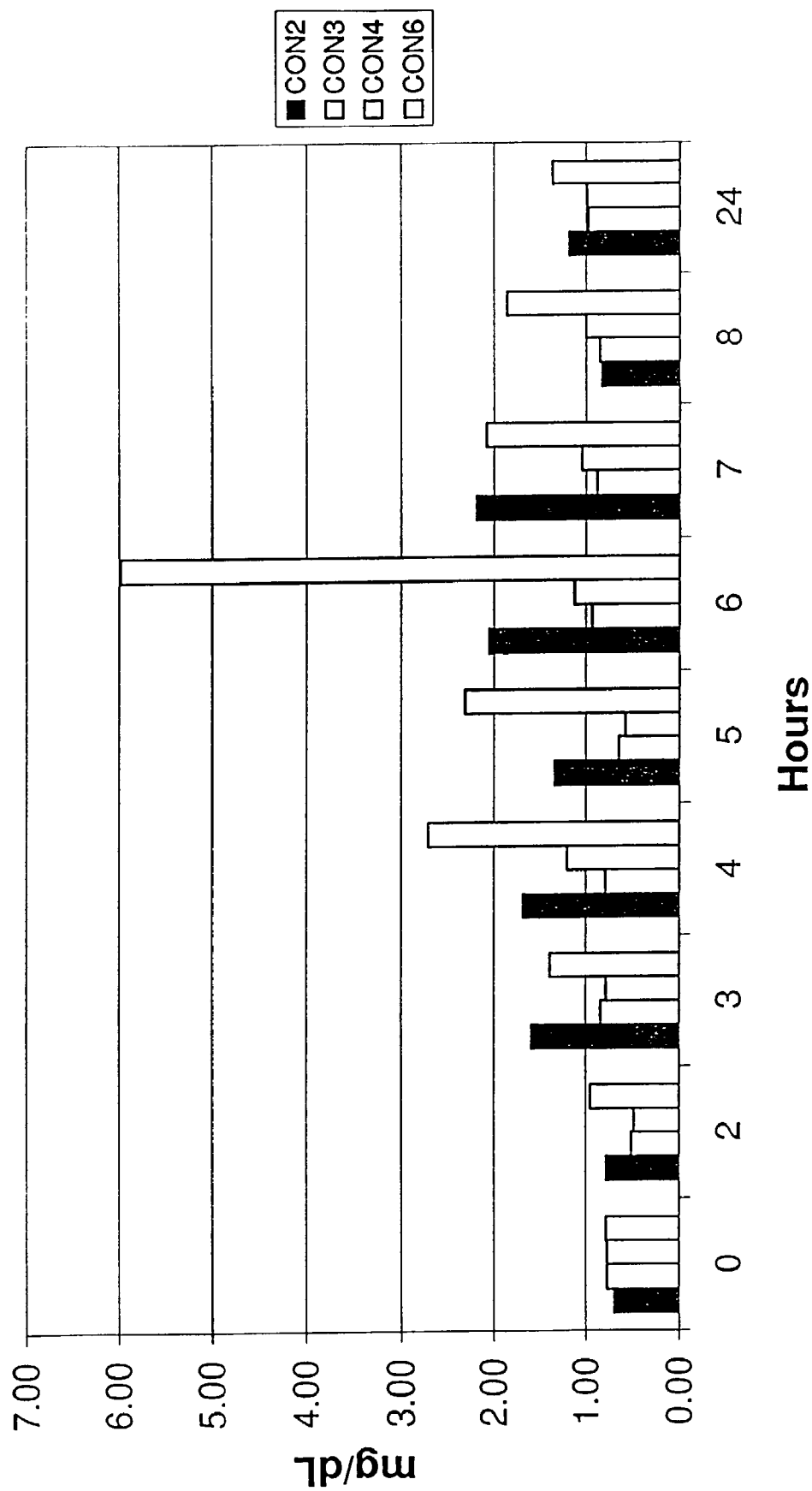
FIG. 4 is a graph showing HA levels in four healthy control subjects taking 30 mg/kg PA and 60 mg/kg THA.
Figure 5A:
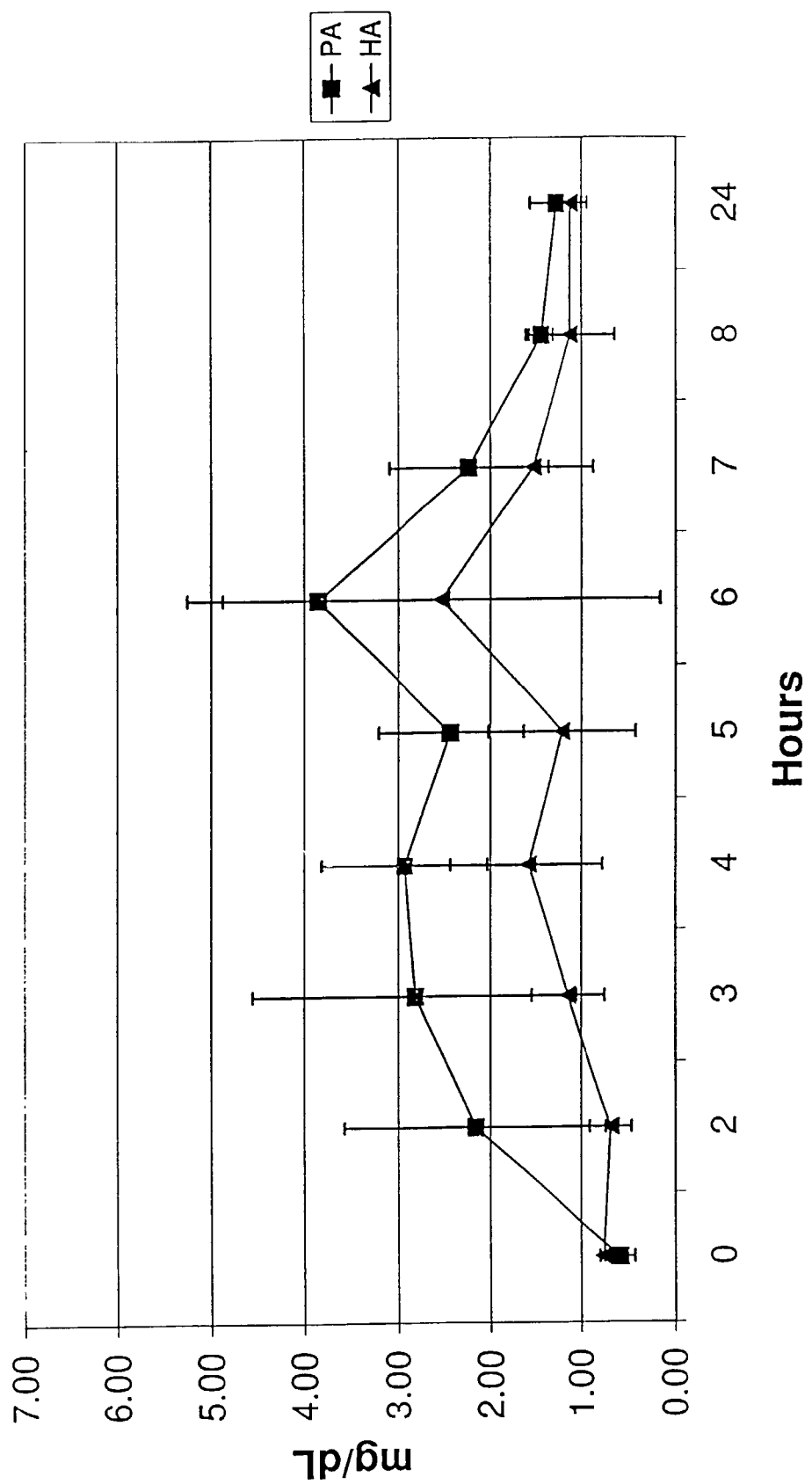
FIG. 5A is a graph showing average fat absorption for four healthy control subjects taking 30 mg/kg PA and 60 mg/kg THA.

The results for HA for the four healthy control subjects corresponding to those described in FIG. 3A are presented for the control subjects taking 30 mg/kg PA and 60 mg/kg THA in FIG. 4. FIG. 5A shows the same results in the aggregate for these four control subjects. For HA, the increase in serum levels was delayed, beginning at 3 hours, with a peak at 6 hours and a decline toward baseline thereafter. HA levels remained lower than PA levels throughout the time period. By 8 hours the PA and HA levels had not returned to baseline, but nearly returned to the levels evident at 24 hours post-dose.

Figure 5B:
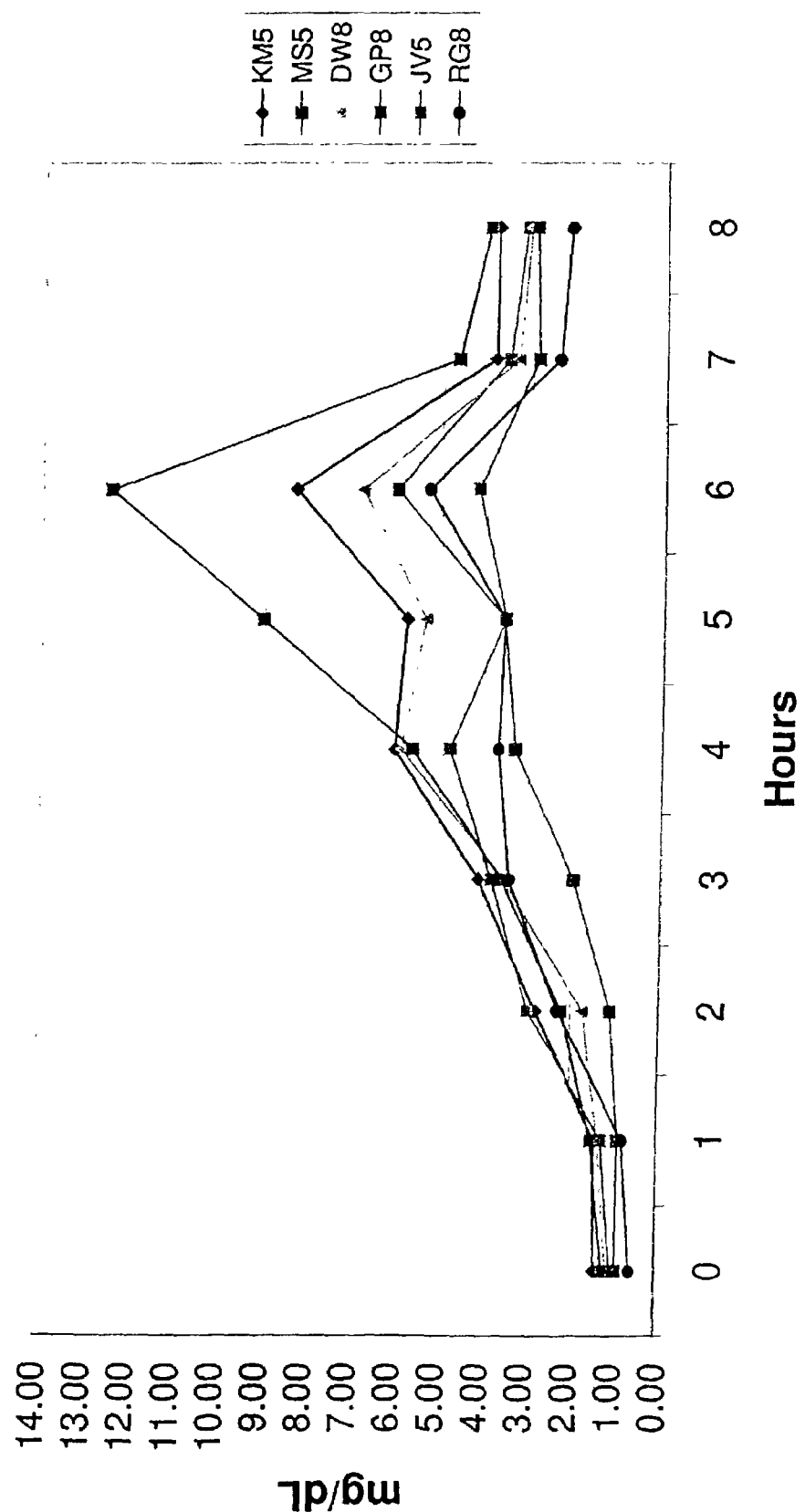
FIG. 5B is a graph showing the average of three separate tests on six healthy subjects taking either a 5.0 gram dose of THA (KM5, MS5 and JV5) or an 8.0 gram dose of THA (DW8, GP8 and RG8).

FIG. 5B illustrates the variability between the average of three tests for each of the six individuals for HA. As for PA, the results indicated that there was variability between individuals in serum response to HA. The pattern of response for HA began to increase after 1 or 2 hours and continued to increase up to 6 hours, with a sharp decrease after that time. The results were similar for individuals receiving 5.0 or 8.0 grams of THA.

Figure 5C:
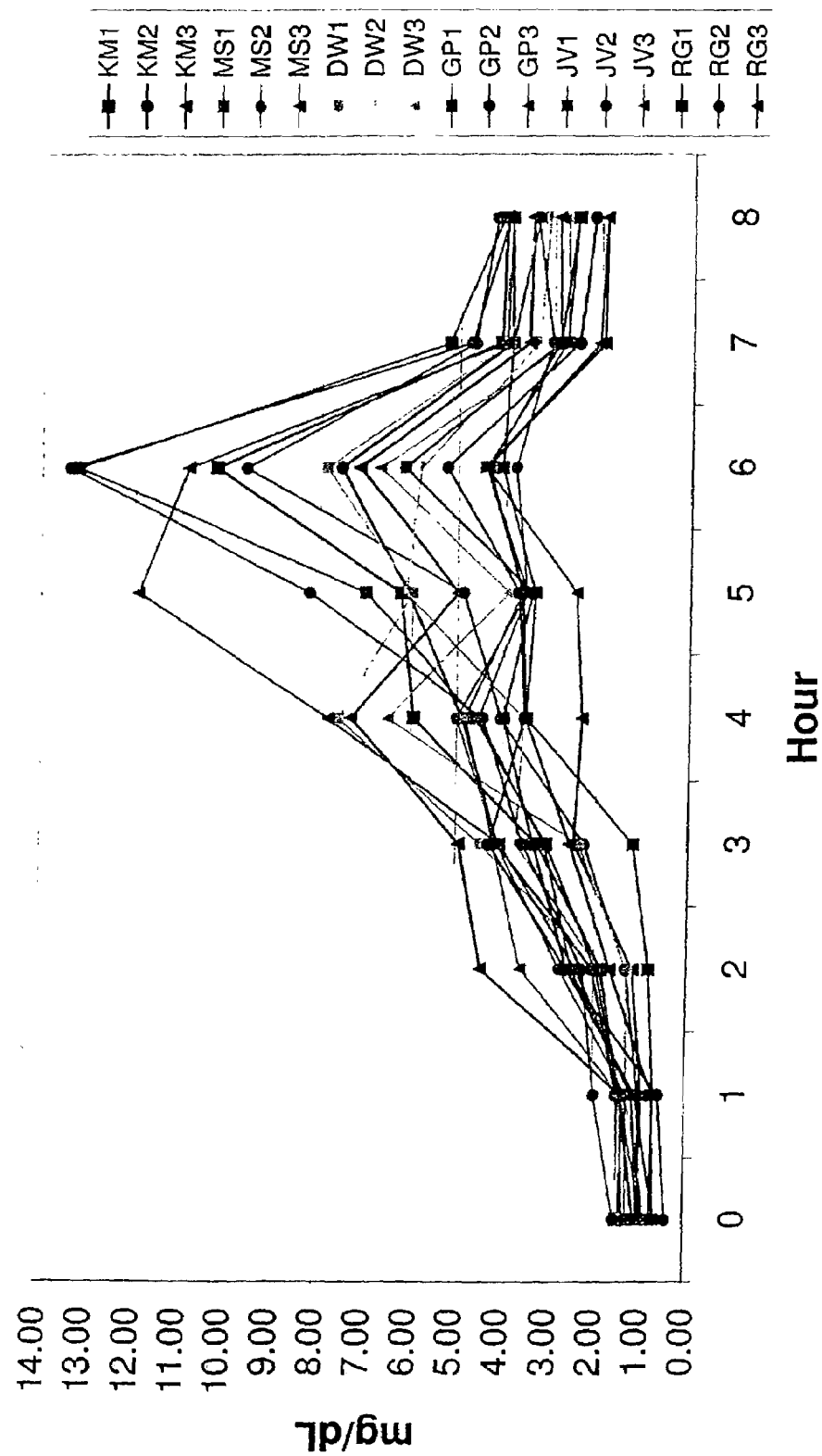
FIG. 5C is a graph showing all of the results from three separate tests on six healthy subjects taking either a 5.0 gram dose of THA (KM, MS and JV) or an 8.0 gram dose of THA (DW, GP and RG).

FIG. 5C shows the results of the three tests for all six individuals. As for PA, there was less variability within individuals measured on separate occasions than there was between individuals. For example, the within-individual standard deviations ranged from 0.2 to 1.1 mg/dL for HA between hours 3 and 6. In contrast, the between-individual standard deviations ranged from 0.7 to 2.9 mg/dL for HA.

Figure 7:
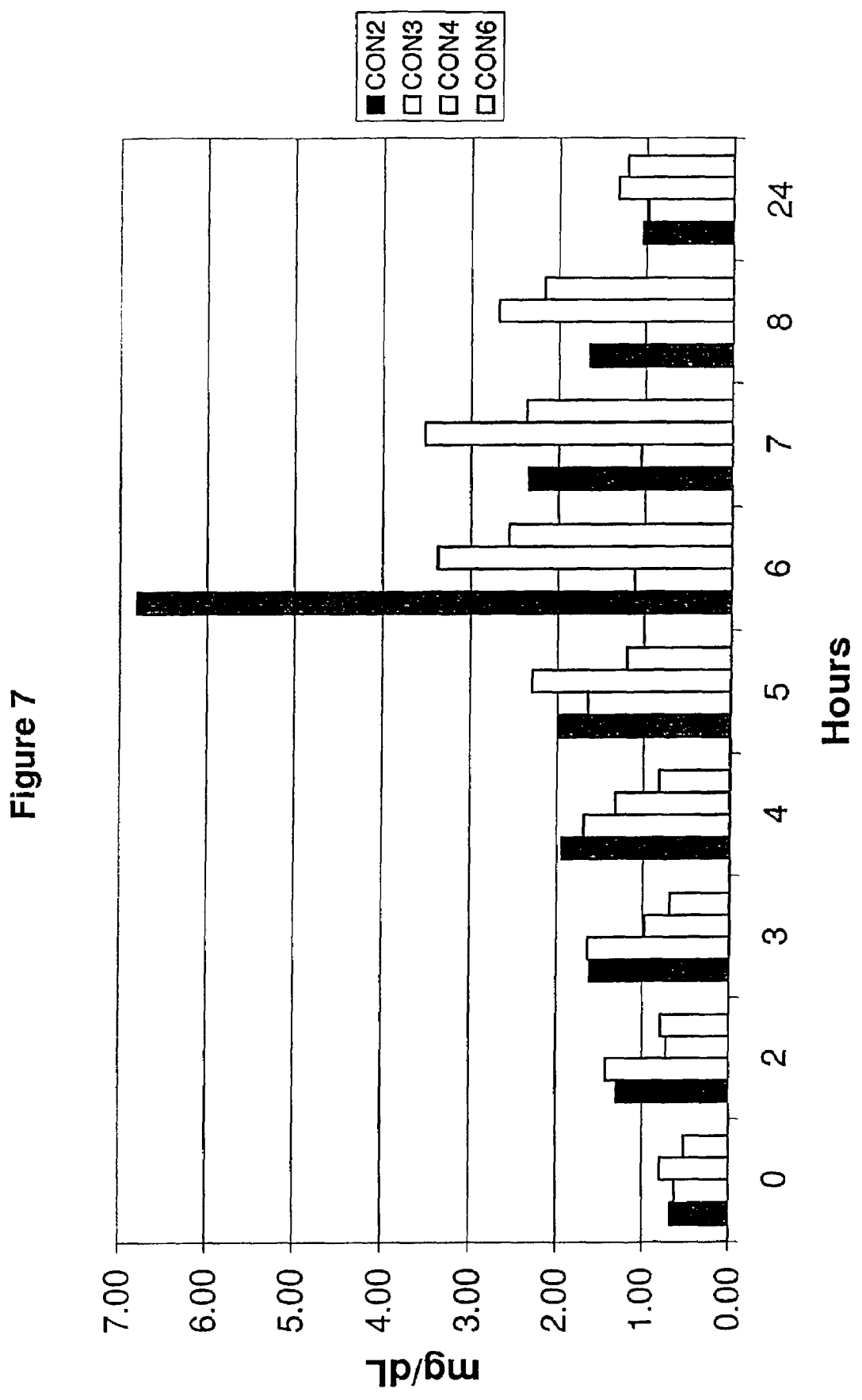
Figure 8:
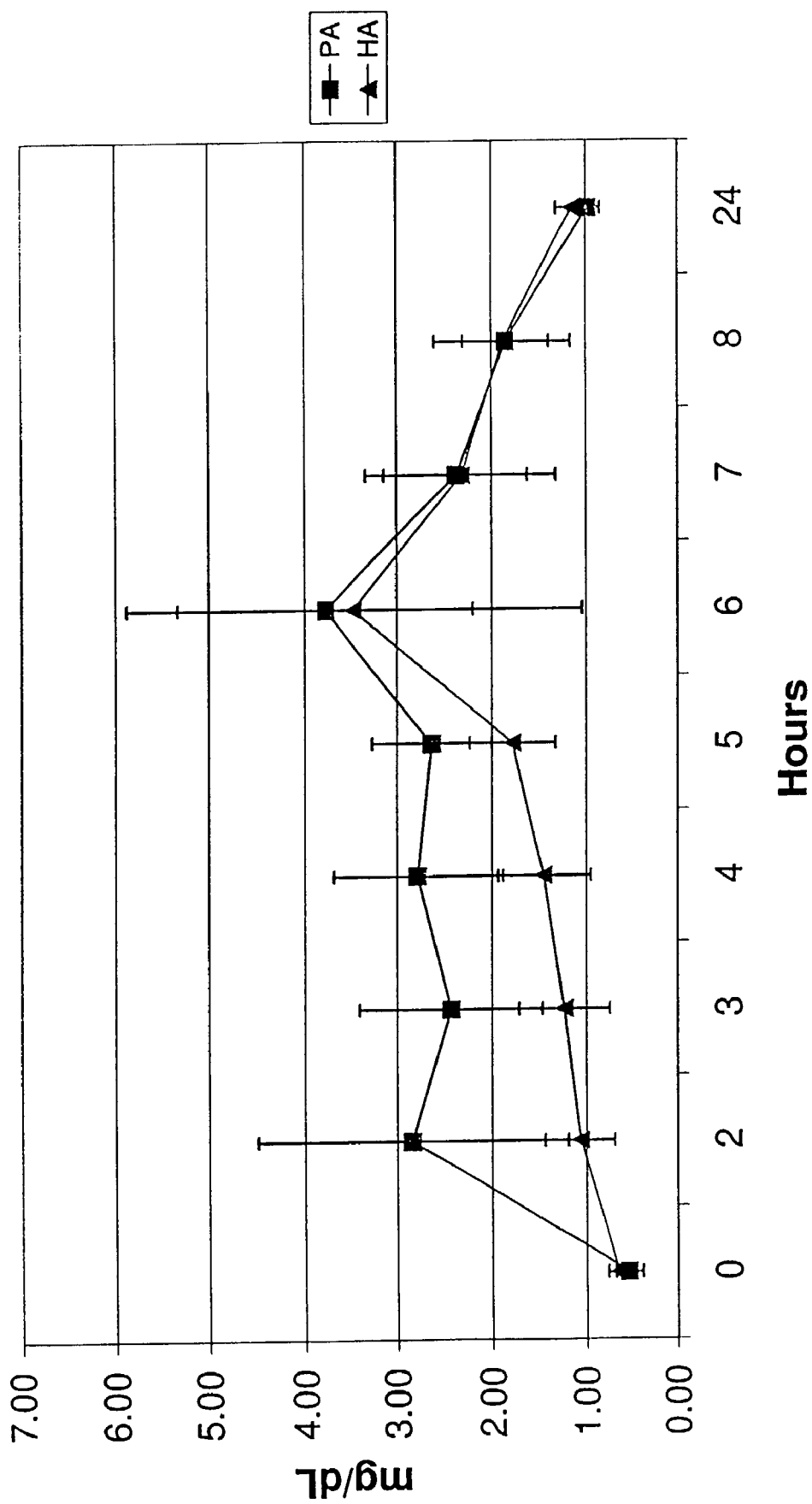
FIG. 8 is a graph showing average fat absorption for four healthy control subjects taking 30 mg/kg PA and 90 mg/kg THA.

The individual results for the same four healthy control subjects of FIG. 3A, FIG. 4 and FIG. 5A after they received 30 mg/kg PA and 90 mg/kg THA are presented in FIG. 6 for PA and FIG. 7 for HA. The average fat absorption for these 4 control subjects is presented in FIG. 8. As when THA was administered at 60 mg/kg, the increase in PA was clearly evident by 2 hours, with a peak at 6 hours, and a decline toward baseline by 8 hours. HA was much slower to increase, with peak levels at 6 hours and a decline thereafter. THA levels remained lower than PA levels during the period of increase and at the peak level.

This test is hereinafter referred to in the Examples as the "Malabsorption Blood Test" (MBT).

EXAMPLE 2

MBT Detects Fat Absorption after Orlistat Treatment

The MBT was further evaluated in healthy adult subjects after treatment with the FDA approved pancreatic lipase inhibitor, orlistat (XENICAL®, Roche Pharmaceuticals, Nutley, N.J.). Orlistat inhibits the absorption of THA which requires hydrolyzation by pancreatic lipase, but not the absorption of PA, which is a free fatty acid. Accordingly, this agent can be used to mimic pancreatic insufficiency in patients.

Subjects

Fifteen healthy adult subject volunteers (9 women) 18 to 50 years of age were recruited through local advertisements. Exclusion criteria included: any chronic illness known to affect nutrient absorption, body mass index (BMI) of less than 21 or greater than 30 kg/in2 (i.e., outside of generally accepted healthy adult ranges), therapy with lipid lowering drugs, diabetes mellitus (NIDDM, IDDM) and disorders associated with altered energy metabolism (e.g., hypothyroidism). This adult age range was selected because orlistat is FDA approved in adults. In addition, adults are able to plan the experimental days for cooperation with four days of the research study diet, outpatient 72-hour stool collection and phlebotomy requirements.

The experiment was conducted in three parts: (1) administration of the MET at baseline; (2) five days of therapy with orlistat 240 mg TID with meals and 72-hour stool collection while on a provided research specific diet; and (3) administration of the MBT on day #6 while on treatment with orlistat. The timeline for the protocol is provided in Table 1.

TABLE 1

Timeline for Pancreatic-Based Fat Malabsorption Studies in Healthy Subjects

| Day of study | Sun. 1 | Mon. 2 | Tue. 3 | Wed. 4 | Th. 5 | Fri. 6 |
|---|---|---|---|---|---|---|
| 8 pm-8 am fast | ▓ | | | | ▓ | |
| 8 am MBT | | ▓ | | | | ▓ |
| Research diet provided | | ▓ | ▓ | ▓ | ▓ | |
| Orlistat (240 mg, TID) | | ▓ | ▓ | ▓ | ▓ | ▓ |
| 72-hour stool collection | | | ▓ | ▓ | ▓ | |

N = 15, healthy, adults aged 18 to 50 years.

Protocol

The objective of the experiment was to derive a measure that describes the rate of absorption of fat using the MBT in healthy adults after pharmaceutically induced pancreatic lipase based fat malabsorption. This measurement is referred to as the coefficient of fat absorption by MBT ($CFA_{MBT}$). A second objective was to compare $CFA_{MBT}$ with CFA obtained by the 72-hour stool and dietary collection method in healthy adult subjects after pharmaceutically induced pancreatic lipase-based fat malabsorption.

Subjects underwent a 12-hour fast from 2100 hours on day #1 of the study. Beginning at the noontime meal of day #1, subjects refrained from non-routine physical activity and avoided all dairy and alcohol intake. Female subjects scheduled their test dates during the first 14 days of their menstrual cycle to standardize the cyclic metabolic and GI motility effects of progesterone. Upon arrival at the study center on the morning of day #2, subjects had their weight and height measured, and an experienced phlebotomist inserted a self-retaining intravenous catheter with a heparin lock for serial blood sampling. Two milliliters of blood was first drawn and held in a sterile syringe; thereafter the experimental blood sample (2 milliliters) was drawn and immediately stored in a 4 milliliter serum separator tube. The blood in the syringe was then reinfused into the subject, followed by a 2 milliliter heparin flush. After the baseline blood samples were obtained, the subjects drank the standardized test breakfast meal within five minutes. Thereafter, serial blood samples were obtained. The number and timing of blood samples was determined by the experiments in Example 1, and was expected to be six or fewer samples over an eight-hour or less time period. During the estimated eight-hour experiment, subjects were permitted to ingest non-caloric and non-caffeinated beverages and ambulation was limited to maintain adherence to the blood-sampling schedule. After completion of the blood sampling on day #2, the catheter was removed, and a snack offered.

Therapy with orlistat

Therapy with oral orlistat 240 mg TID began on day #2 at the lunch meal immediately after completion of the MBT. It was administered three times a day before meals and continued throughout the administration of the second MBT breakfast on day #6.

Research Study Diet

A specific research study diet was required for determination of CFA using the 72-hour stool collection method. Three daily meals and snacks providing approximately 80 g of fat per day were provided to each subject. The meals were pre- and post-weighed to obtain an accurate dietary intake record. Subjects were required to return all remainders of meals to the study center. Subjects were also required not to consume any other food or beverages apart from the research study diet. Other than the research study diet, subjects were only permitted to drink non-caloric and non-caffeinated beverages such as water or diet soda. The research study diet started with lunch on day #2 and proceeded until dinner on day #5. Breakfast on day #5 consisted of the MBT breakfast drink.

72-Hour Stool Collection Method

The 72-hour stool collection method was conducted on an outpatient basis while the subjects were on the research study diet and being treated with orlistat. The stool collection started at 0700 hours on day #3 and was completed at 0700 hours on day #6. Detailed verbal and written instructions and supplies for the stool collections were given to the subjects by a research team.

Administration of the second MET was conducted on the morning of day #6 while the subjects were ingesting orlistat. Subjects completed a 12-hour overnight fast starting at 2000 hours on day #5. Subjects were admitted to the outpatient study center and the MBT was administered according to the protocol on day #2 at 0800 hours.

Results

Figure 9:
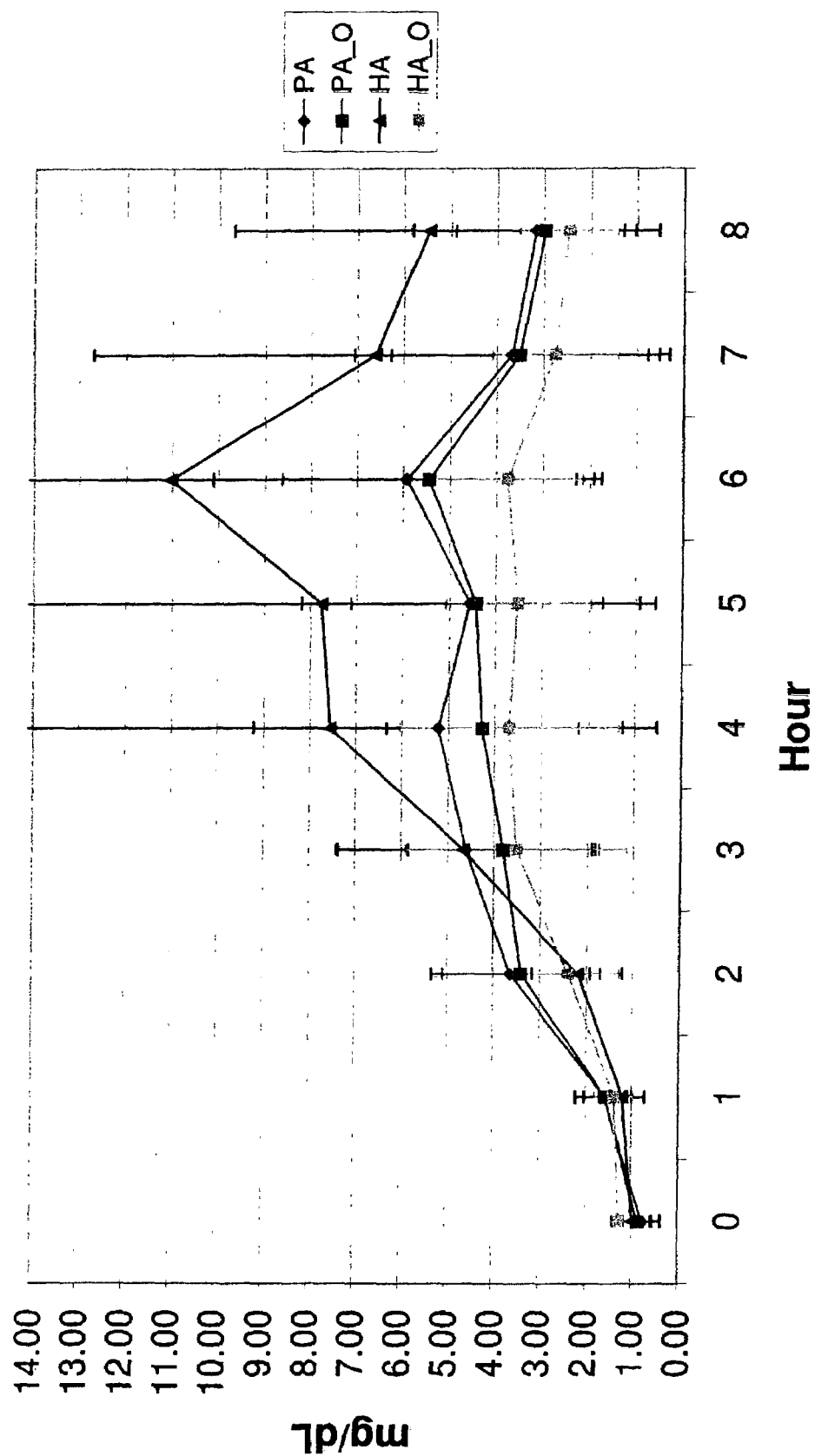
FIG. 9 is a graph showing the average results before and after orlistat treatment from fifteen subjects. The subjects were given fixed doses of PA (2.5 grams) and THA (8.0 grams).

FIG. 9 illustrates the average response of PA and HA before and after orlistat for all fifteen subjects, including those which were found to be high absorbers of fat. As anticipated, the serum response of PA was similar for the twelve healthy subjects both prior to and after receiving orlistat (FIG. 9). However, the serum response of HA without orlistat treatment was clearly higher than after administration of orlistat. From hours 3 through 6, the magnitude of absorption of HA while on orlistat ranged from approximately 50% to 75% of the magnitude of absorption without orlistat in these subjects. These results demonstrate that the MBT detected the fat malabsorption induced by orlistat in healthy subjects.

Figure 10:
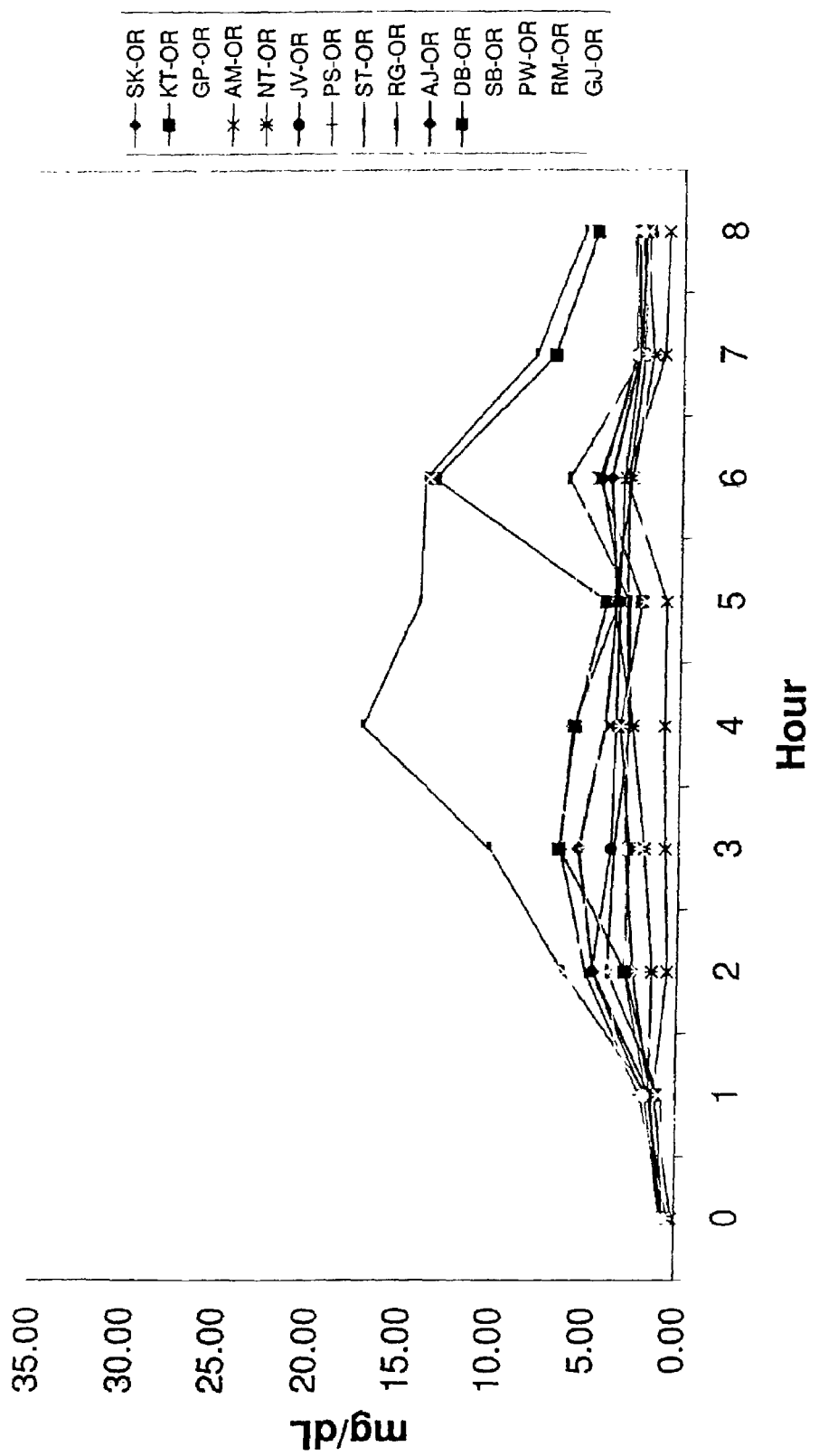
FIG. 10 is a graph showing the results of PA absorption prior to orlistat treatment from fifteen subjects. The subjects were given fixed doses of PA (2.5 grams) and THA (8.0 grams).
Figure 11:
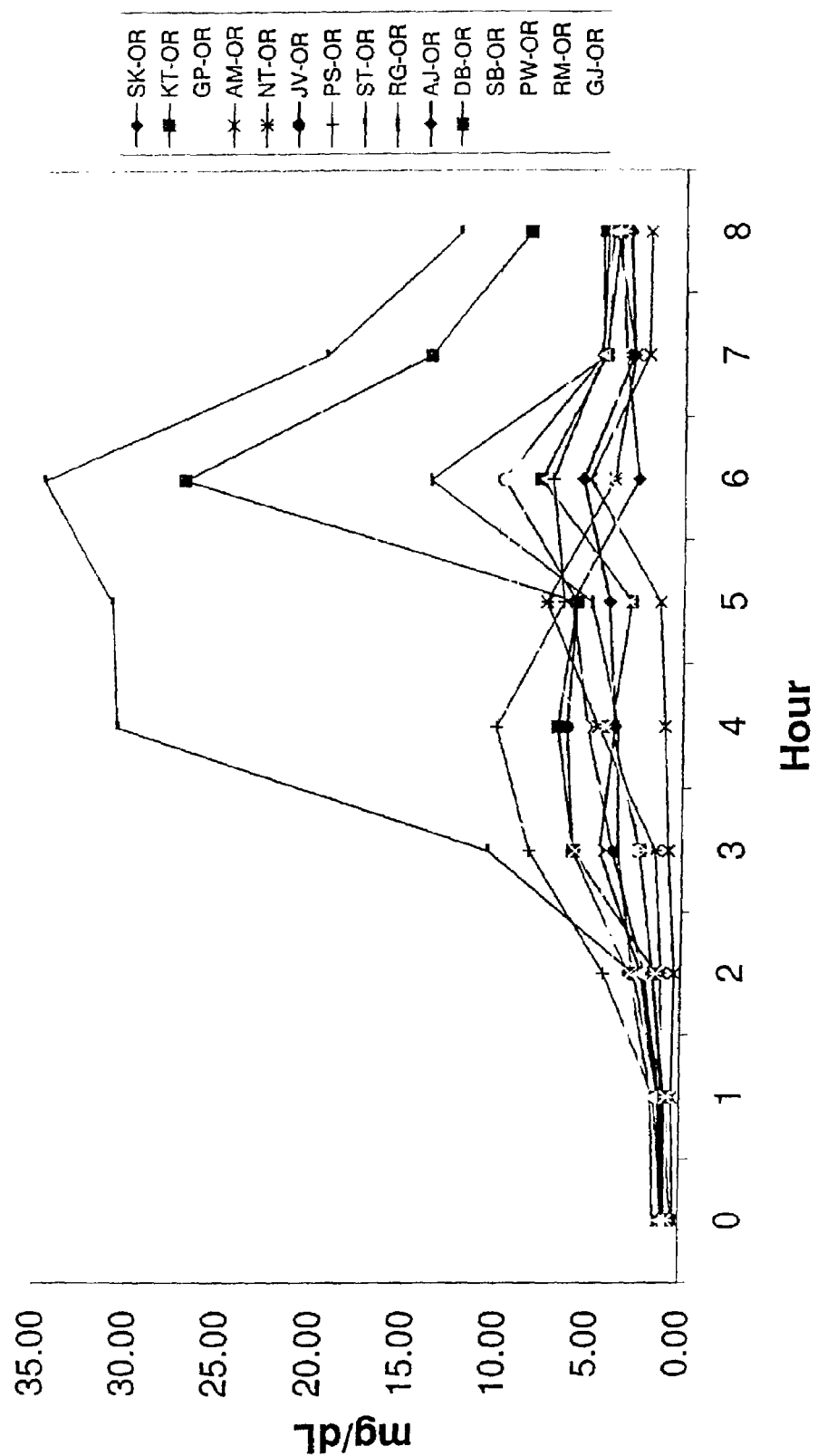
FIG. 11 is a graph showing the results of HA absorption prior to orlistat treatment from fifteen subjects. The subjects were given fixed doses of PA (2.5 grams) and THA (8.0 grams).
Figure 12:
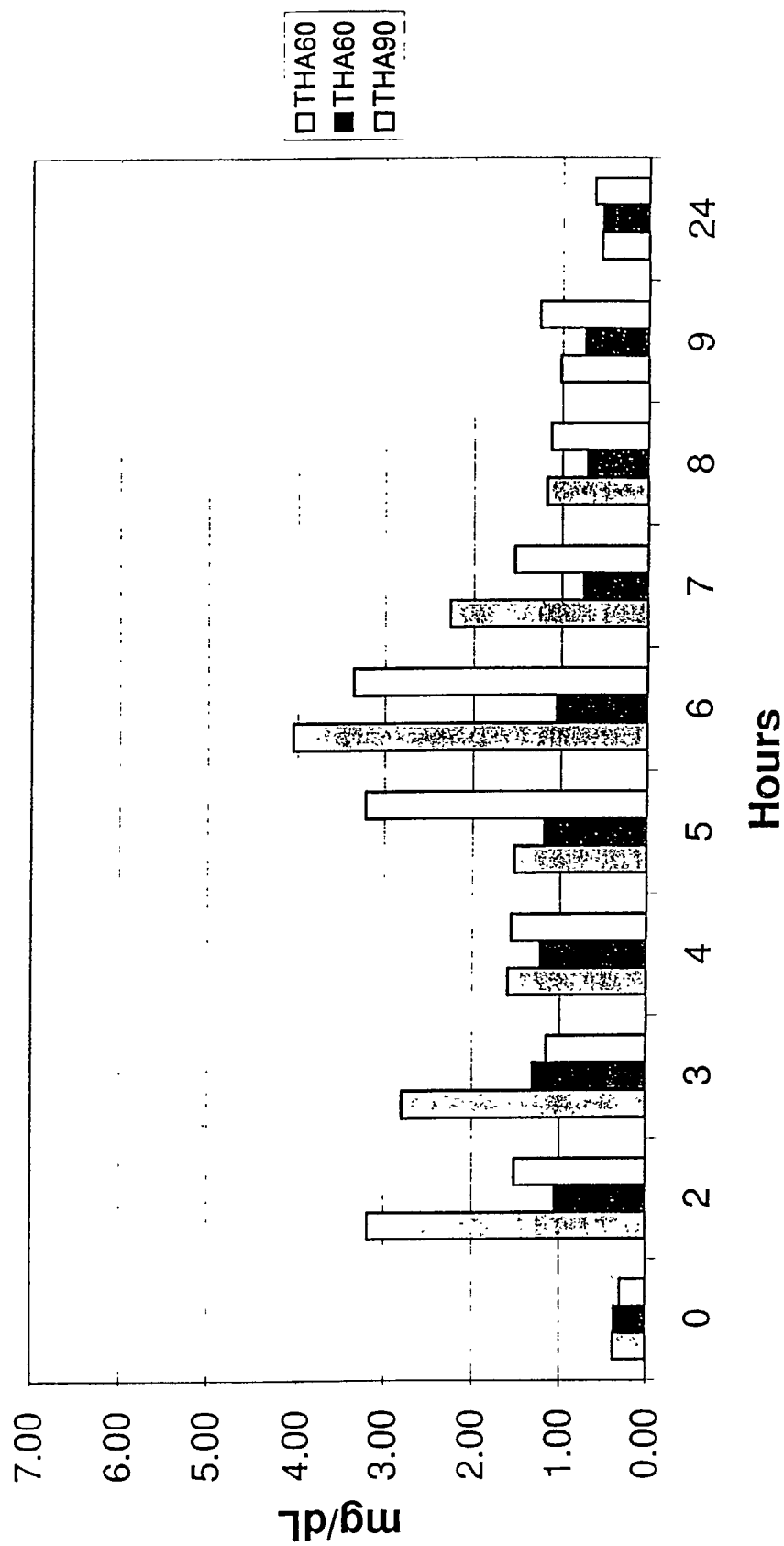
FIG. 12 shows PA levels in three subjects with cystic fibrosis taking 30 mg/kg PA and either 60 mg/kg THA (n=2) or 90 mg/kg THA (n=1), while on their usual pancreatic enzyme therapy.
Figure 13:
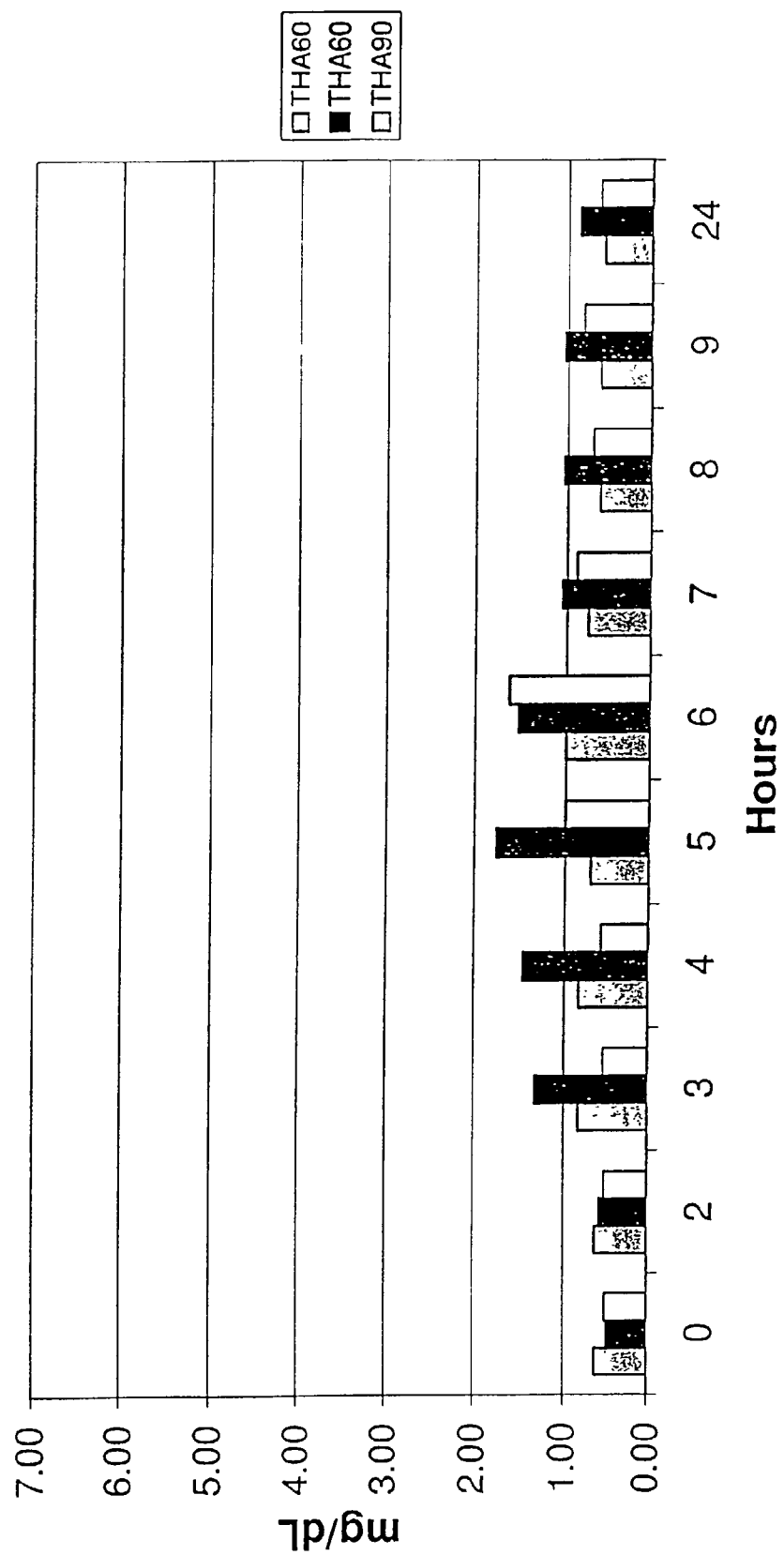
FIG. 13 is a graph showing HA levels in three subjects with cystic fibrosis taking 30 mg/kg PA and either 60 mg/kg THA (n=2) or 90 mg/kg THA (n=1), while on their usual enzyme therapy.
Figure 14:
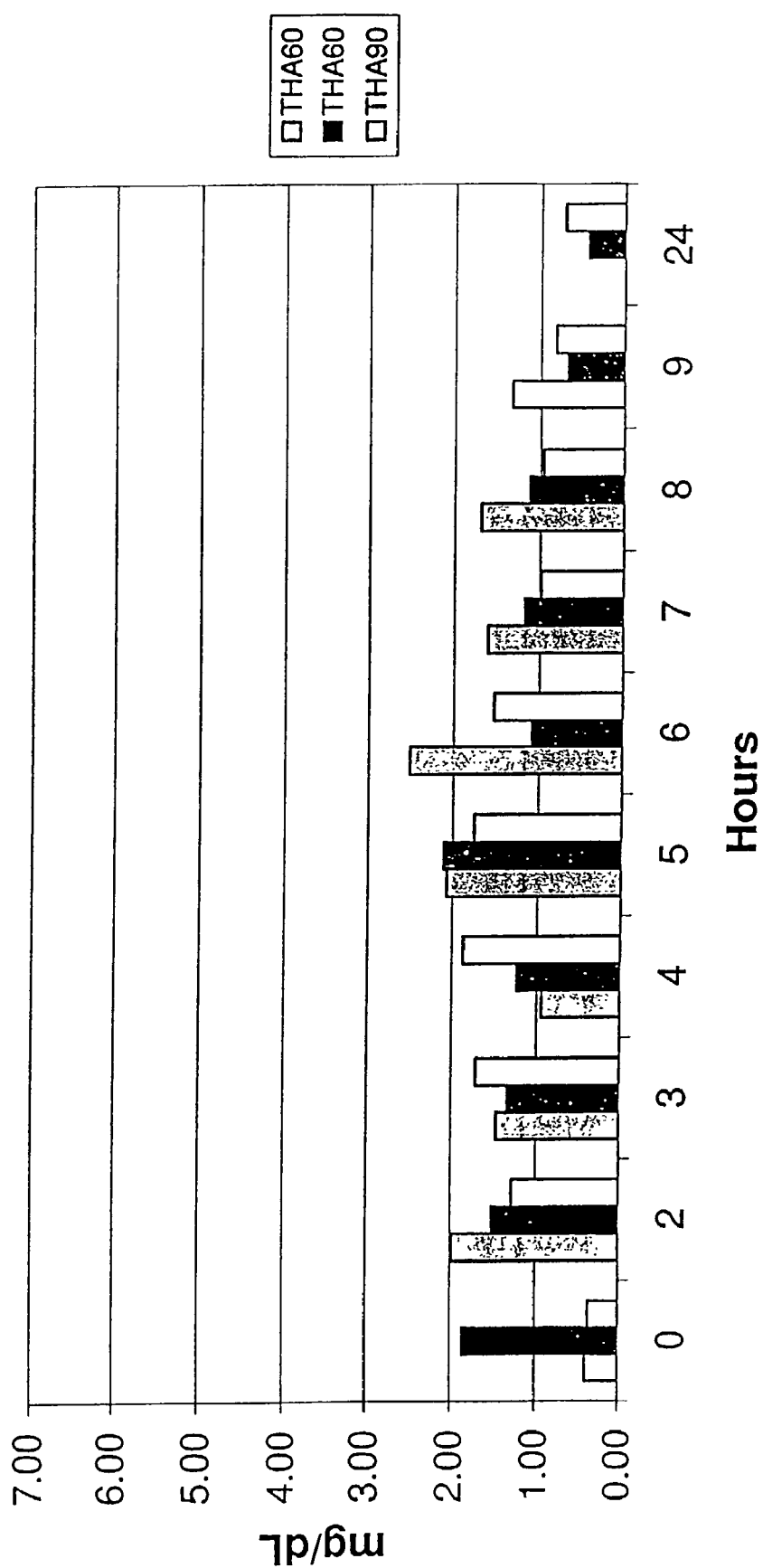
FIG. 14 shows PA levels in three subjects with cystic fibrosis taking 30 mg/kg PA and either 60 mg/kg THA (n=2) or 90 mg/kg THA (n=1) with no pancreatic enzymes.
Figure 15:
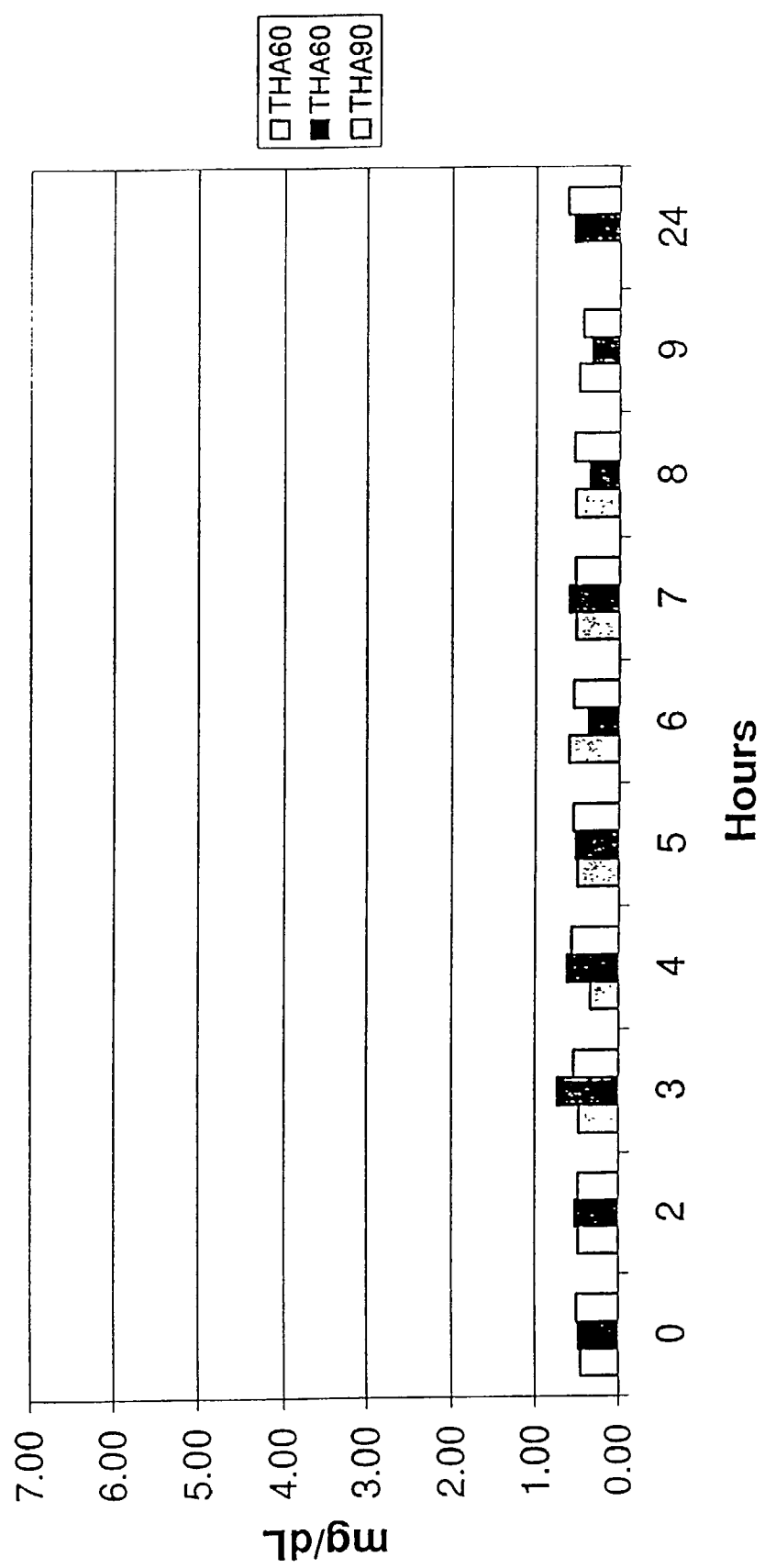
FIG. 15 is a graph showing HA levels in three subjects with cystic fibrosis taking 30 mg/kg PA and either 60 mg/kg THA (n=2) or 90 mg/kg THA (n=1) with no pancreatic enzymes.

FIGS. 10 and 11 show the individual responses of PA and HA, respectively, prior to orlistat with the high absorbers included. The difference in magnitude for the high absorbers was obvious. The average absorption of PA was approximately 65% and for HA approximately 45%. However, for the high absorbers, it was closer to 90-100% for both fats.

EXAMPLE 3

Pancreatic-Based Fat Malabsorption Studies Involving Subjects with CF and Pancreatic Insufficiency A Cystic Fibrosis (CF) dosing study was performed to determine the serum response pattern of PA and THA in subjects with Cystic Fibrosis (CF) and pancreatic insufficiency. It was hypothesized that the temporary withdrawl of pancreatic enzymes would result in malabsorption of THA, but not PA.

Subjects

Subjects with CF and pancreatic insufficiency currently treated with pancreatic enzymes, aged greater than 8 years were recruited. Exclusion criteria included: forced expiratory volume of the lungs at 1 second (FEV1) <40%, a history of fibrosing colonopathy or significant bowel resection (>10 cm), mental retardation, significant neurological deficit, developmental disability and autism. Subjects are in their usual state of good health. This age range was selected because it includes children during active growth where information regarding degree of malabsorption leads to improved nutritional intervention and pancreatic enzyme therapy. Also, children greater than 8 years of age are mature enough to provide assent and feedback concerning acceptability and tolerance of the MBT.

Results

In the experiments shown in FIGS. 12 through 15, three subjects with CF were given either 30 mg/kg PA and 60 mg/kg THA (2 subjects) or 30 mg/kg PA and 90 mg/kg THA (1 subject) in a digestible composition consisting of a liquid breakfast shake after a 12 hour fast. The subjects were tested while they were taking their usual doses of pancreatic enzymes and then were tested again (more than one week later) when they were not taking pancreatic enzymes. Blood was sampled at baseline and then at hourly intervals from 2 to 8 hours and then sampled again at 24 hours. Subjects were fed a prepared lunchtime meal with a known quantity of fat (80 grams). The individual results for fat absorption for the 3 subjects with CF on enzymes are presented in FIG. 12 for PA and FIG. 13 for HA. For the same 3 subjects with CF off enzymes, the results for fat absorption are presented in FIG. 14 for PA and FIG. 15 for HA.

Figure 16:
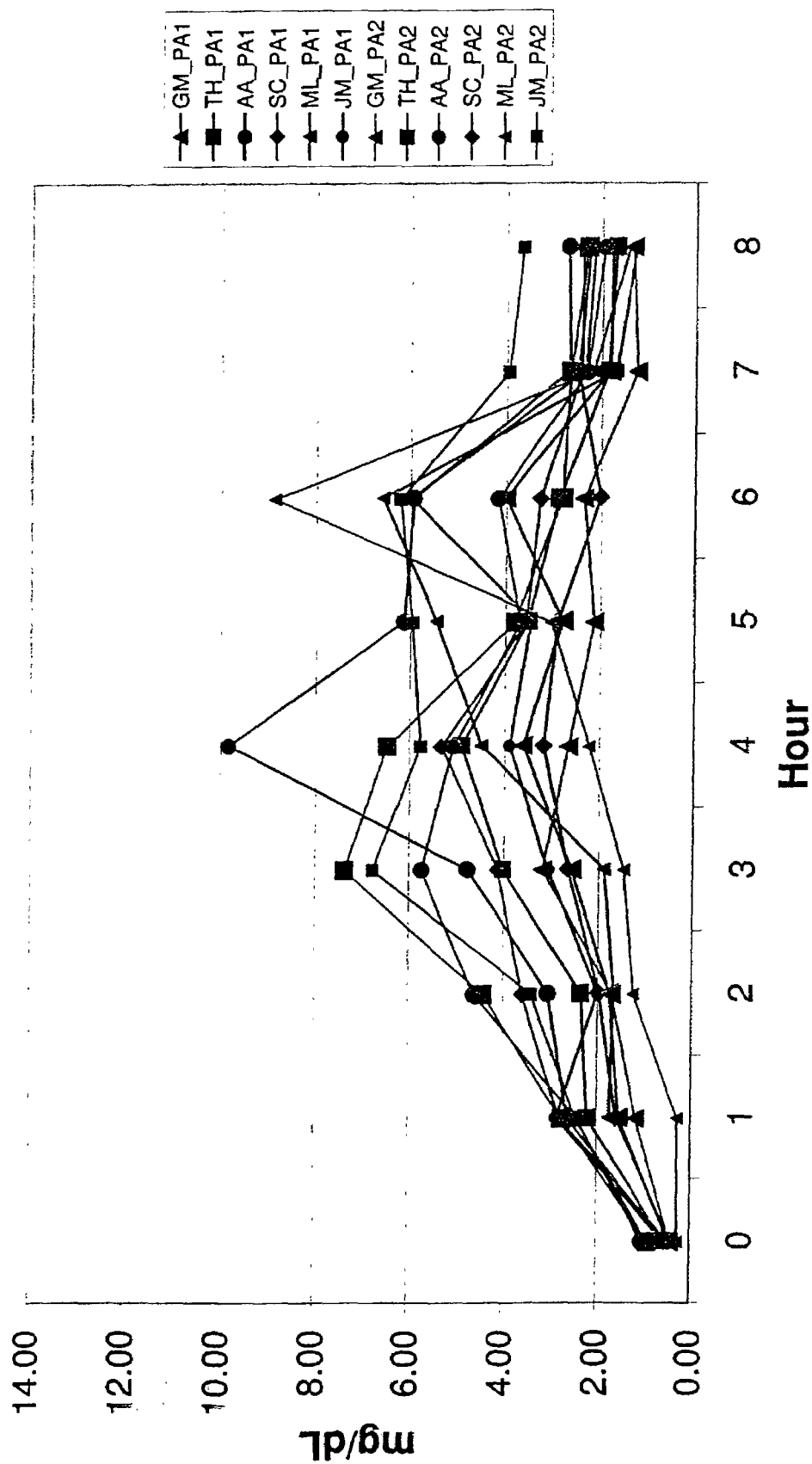
FIG. 16 is a graph showing PA serum levels in six subjects with CF both on (PA1) and off (PA2) pancreatic enzyme treatment. The subjects with CF were given fixed doses of PA (2.5 grams).
Figure 17:
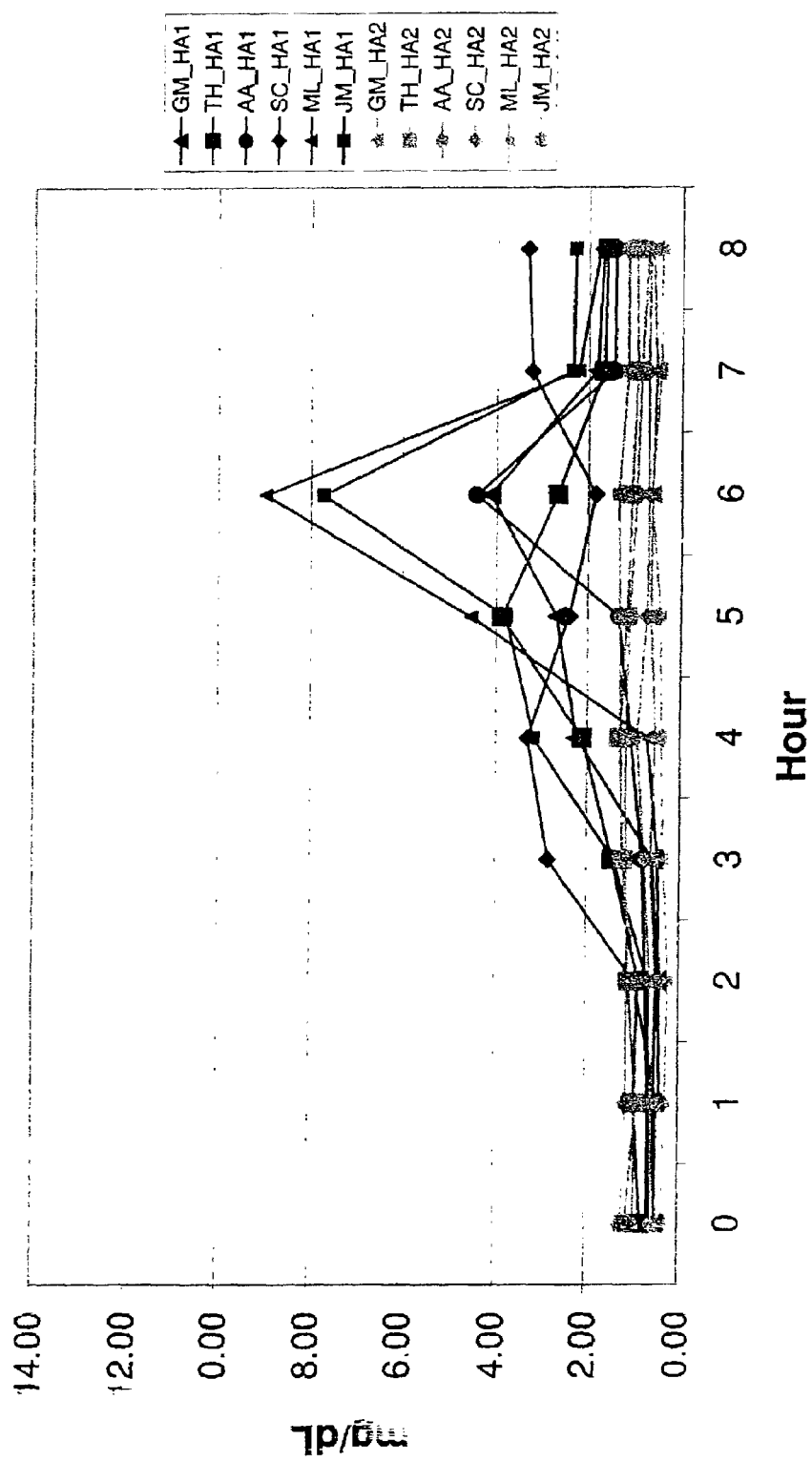
FIG. 17 is a graph showing HA serum levels in six subjects with CF both on (HA1) and off (HA2) pancreatic enzyme treatment. The subjects with CF were given either 5 grams of THA (subjects GM, AA and ML) or 8 grams of THA (subjects TH, SC and JM).
Figure 18:
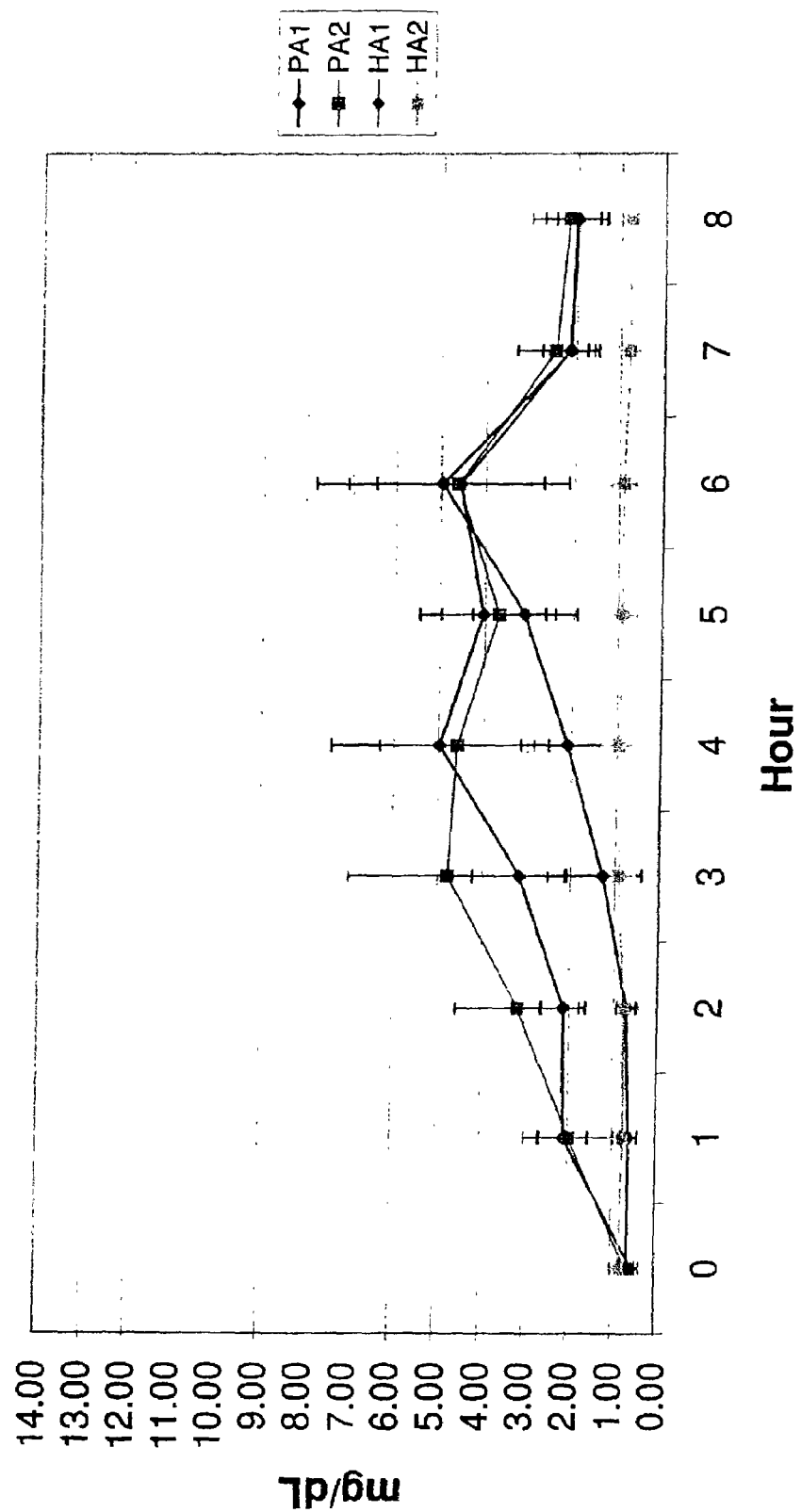
FIG. 18 is a graph showing the average PA and HA serum levels from FIGS. 16 and 17 for the six subjects with CF while on (1) or off (2) pancreatic enzyme treatment.

Additional experiments were performed on six subjects with CF either on or off pancreatic enzyme treatment. The serum levels of PA and HA in these six subjects on and off pancreatic enzyme treatment are presented in FIG. 16 and FIG. 17, respectively. The average serum levels for PA and HA in the six subjects on and off pancreatic enzyme treatment are presented in FIG. 18.

For subjects with CF on enzymes, the increase in PA absorption was evident by hour 2, with a plateau from approximately 2 to 6 hours, followed by a decline close to baseline levels by hour 8. For HA, after a 2 hour delay, serum levels increased slowly with a peak at approximately 6 hours and a decline thereafter. Serum levels of both PA and HA in the subjects with CF taking enzymes were lower than those seen in the healthy control subjects. For subjects with CF off enzymes, PA levels increased by hour 2 with a plateau from approximately 3 to 6 hours and a decline thereafter. To the contrary, in subjects with CF off enzymes, there was no increase in serum levels of HA, which remained low throughout the test period.

Figure 19:
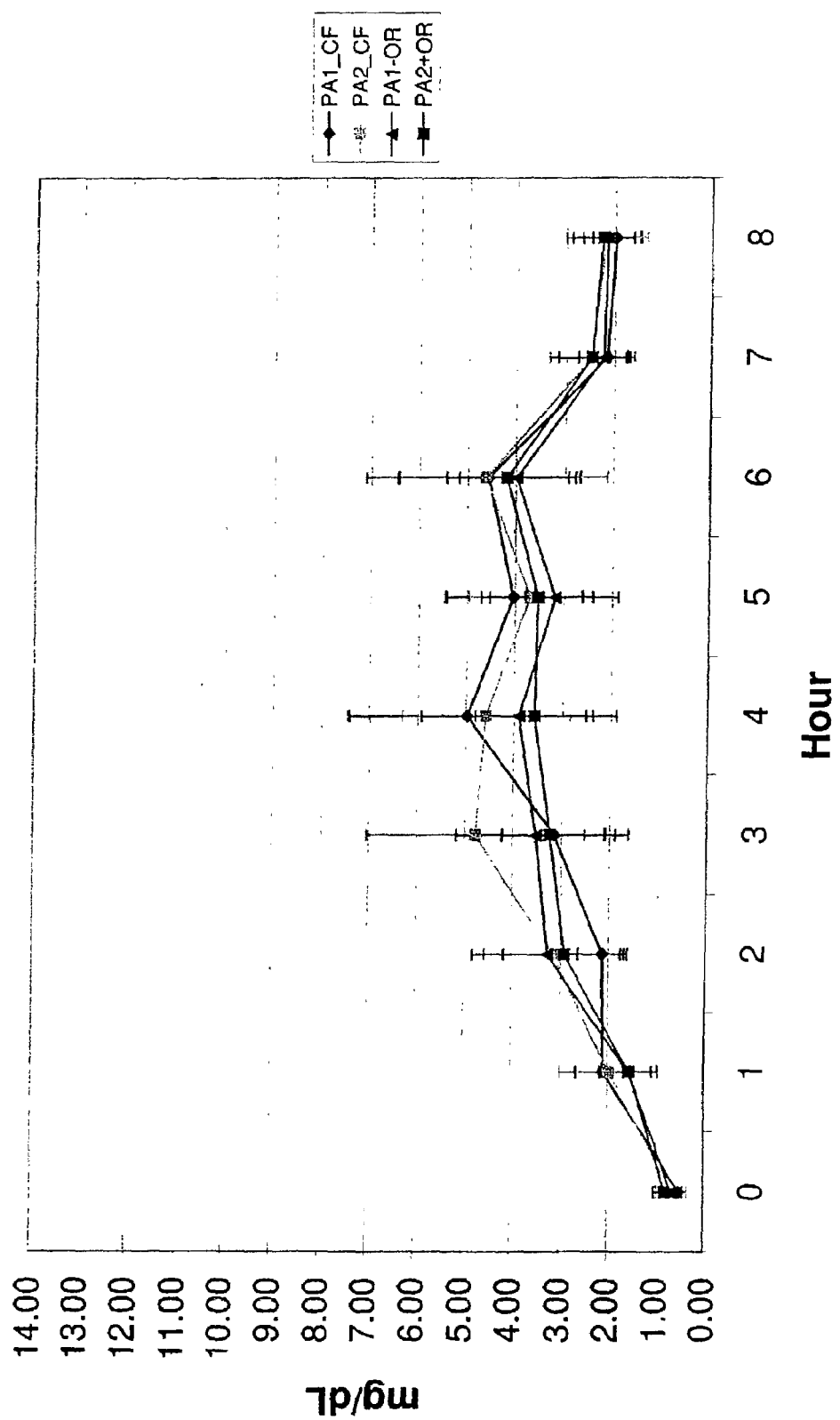
FIG. 19 is a graph showing the average PA serum levels in six subjects with CF on and off pancreatic enzyme treatment and twelve healthy subjects on or off orlistat treatment.
Figure 20:
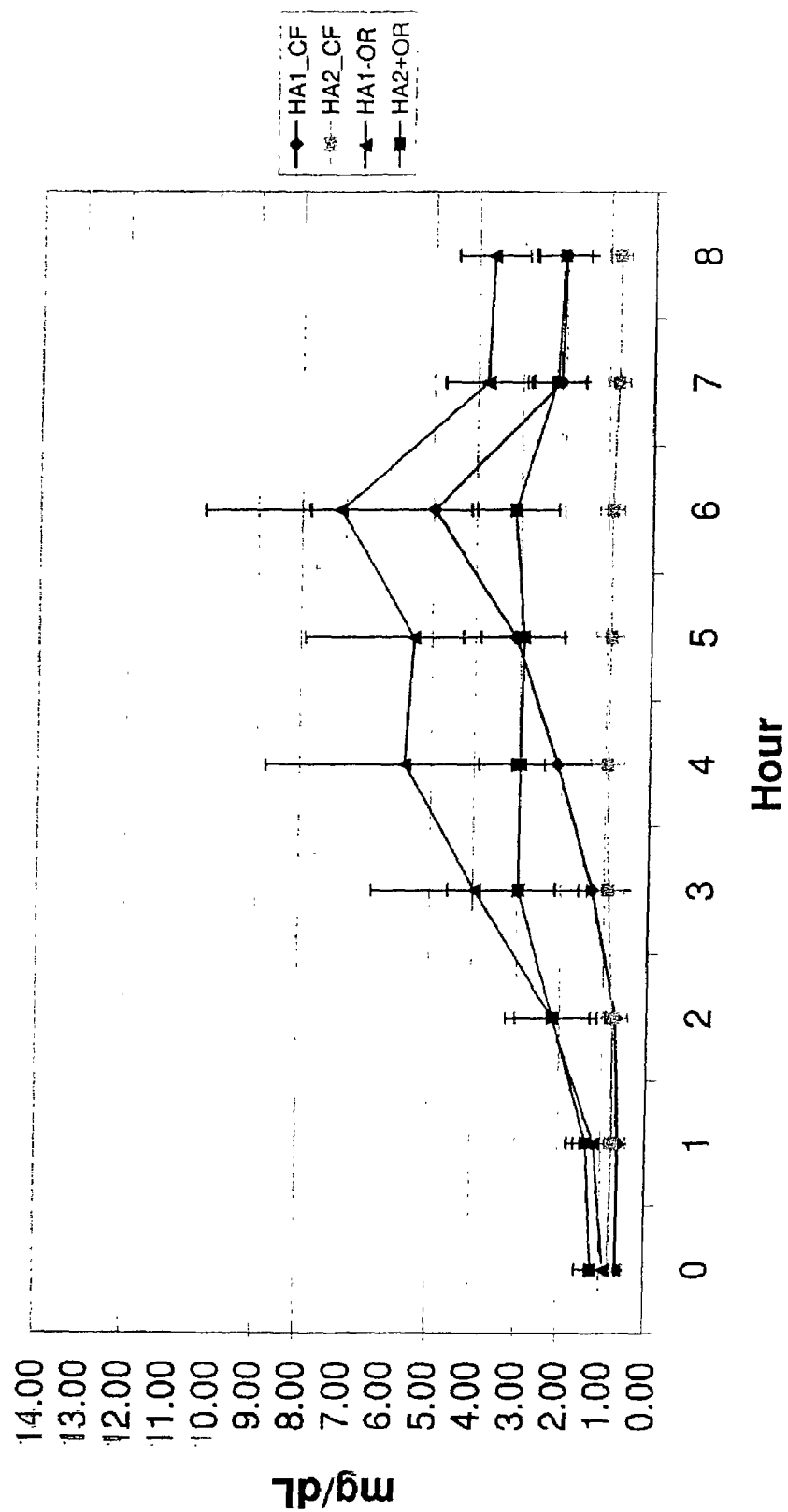
FIG. 20 is a graph showing the average HA serum levels in six subjects with CF on and off pancreatic enzyme treatment and twelve healthy subjects on or off orlistat treatment.

In additional experiments, serum PA and HA levels were compared in healthy subjects on and off orlistat treatment and subjects with CF on and off pancreatic enzyme therapy. The data are presented for levels of PA and HA in FIGS. 19 and 20, respectively.

Discussion

Patterns of PA adsorption were similar in subjects with CF and healthy subjects whether on or off pancreatic enzyme medication or whether before or after orlistat treatment. As expected, PA adsorption was not affected by either the lack of pancreatic lipase or pharmaceutically induced pancreatic insufficiency.

However, patterns of HA absorption were somewhat different between subjects with CF on normal enzyme therapy and healthy subjects before orlistat treatment. In CF subjects, the adsorption of HA was delayed and was of lower magnitude compared to healthy controls. These results demonstrated that the MET can detect reduced fat absorption in CF subjects even with enzyme therapy compared to healthy controls.

EXAMPLE 4

Proposed Inpatient Study for Assessing MBT in Subjects with CF

The protocol will be conducted in two parts, addressing objectives 1 and 2 separately. Objective 1 involves a 5-day inpatient admission (day #1 to #5). Objective 2 involves an outpatient visit that will be scheduled after a minimum period of seven days following completion of Objective 1. The timeline for the studies of Objectives #1 and #2 is provided in Table 2.

TABLE 2

Timeline for Studies in Subjects with CF for Objectives #1 and #2.

| Day of study | 1 | 2 | 3 | 4 | 5 | 6-10 | 11 | 12 |
|---|---|---|---|---|---|---|---|---|
| CRC | | | | | | | | |
| 8 pm-8 am fast | | | | | | | | |
| 8 am MBT | | | | | | | | |
| Research study diet | | | | | | | | |
| 72 hour stool collect | | | | | | | | |
| Routine enzymes | | | | | | | | |
| Reduced enzymes | | | | | | | | |

The first objective of these studies will be to compare $CFA_{MBT}$ with CFA derived from the 72-hour stool and dietary collection method in subjects with CF and pancreatic insufficiency receiving their prescribed routine doses of enzyme therapy (baseline).

Subjects will be admitted to the inpatient study center from day #1 to #5 (four nights). During the stay, all food and beverage intake will be documented (pre- and post- weights of meals are taken), and a 72-hour stool collection test will be conducted during their routine doses of pancreatic enzymes. The MBT will be performed at the end of the diet and stool collection on day #5 and #6.

Anthropometric assessment (weight, height, skin fold measurements) will be performed and FEV-1 data will also be obtained. Starting on day #1, subjects will be provided a diet designed to maintain their weight, and containing about 35% of calories from fat. After conversing with the patient and family to determine food preferences and usual food intakes, a nutritionist will design the diet. The study center staff will provide detailed instructions and equipment regarding stool collections. On the morning of day #5, the MBT will be administered while subjects are taking their routine doses of pancreatic enzymes. The MBT will be administered as described in Example 1 after a 12-hour overnight fast starting at 2000 hrs on day #4. After completion of the MBT, subjects will be discharged home.

The second objective of these studies will be to examine how $CFA_{MBT}$ responds when the pancreatic enzyme dose is randomly reduced from baseline to 0% or 50% of the routine dose for two meals (dinner and MBT breakfast test meal) in these subjects with CF and pancreatic insufficiency.

Subjects in the Objective 2 experiment will be randomized to receive one of two reduced doses of pancreatic enzymes: 0% or 50% of their prescribed routine dose starting with the dinner meal on day #11. Following the standard 12-hour overnight fast, the subjects will be admitted to the outpatient study center and the MBT will be administered with the assigned pancreatic enzyme dose. After completing the MBT, subjects will be discharged from the CRC after being instructed to resume their prescribed doses of routine pancreatic enzymes.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of diagnosing pancreatic-based fat malabsorption disorder in a mammal comprising the steps of:
   a) obtaining a baseline sample of blood from said mammal;
   b) administering to said mammal a digestible composition comprising a free fatty acid which can be absorbed from the small intestine of the mammal in the absence of pancreatic lipase hydrolysis thereof and a triglyceride which cannot be absorbed from the small intestine of the mammal in the absence of pancreatic lipase hydrolysis thereof;
   c) obtaining at least one subsequent sample of blood from said mammal following administration of said digestible composition;
   d) assaying said baseline sample and said at least one subsequent sample for said free fatty acid and the fatty acids of said triglyceride;
   e) determining from step d) the rate of fatty acid absorption of each of said free fatty acid and the fatty acids of said triglyceride in said mammal thereby obtaining a first absorption profile; and
   f) comparing the first absorption profile with a second profile of fatty acid absorption obtained after carrying out steps a), b) and c) on a control mammal being positive or negative for a pancreatic-based fat malabsorption disorder, whereby the presence of a pancreatic-based fat malabsorption disorder in said mammal is indicated when said first absorption profile is comparable to said second absorption profile obtained from a control mammal being positive for said pancreatic-based fat malabsorption and the absence of a pancreatic-based fat malabsorption disorder in said mammal is indicated when said first absorption profile is comparable to said second absorption profile obtained from a control mammal being negative for said pancreatic-based fat malabsorption disorder;
   wherein both said free fatty acid and said triglyceride are not radiolabeled; and
   wherein said free fatty acid has an odd number of carbons and said triglyceride comprises fatty acids having an odd number of carbons.

2. The method of claim 1 wherein both said free fatty acid and said triglyceride are detectably labelled.

3. The method of claim 1, wherein said mammal is a human.

4. The method of claim 1, wherein said positive control mammal has a pancreatic-based fat malabsorption disorder which is the result of a deficiency in pancreatic lipase.

5. The method of claim 1, wherein said disease associated with fat malabsorption disorder is selected from the group consisting of cystic fibrosis, hereditary pancreatitis, α1 antitrypsin deficiency, Shwachman Syndrome, Johanson-Blizzard Syndrome, sideroblastic anemia, pancreatic insufficiency, lipase deficiency, co-lipase deficiency in children, both partial and complete pancreatic surgical resection, pancreatic cancer, chronic and autoimmune pancreatitis, hyperlipidemia, and hyperparathyroidism.

6. The method of claim 1, wherein said free fatty acid is a saturated, long-chain free fatty acid and said triglyceride comprises one or more saturated, long-chain fatty acids.

7. The method of claim 6, wherein said saturated long-chain free fatty acid is pentadecanoic acid (PA) and said triglyceride is triheptadecanoin (THA).

8. The method of claim 6, wherein the free fatty acids resulting from the digestion and/or absorption of said substrates are PA and heptadecanoic acid (HA).

9. The method of claim 1, wherein said assaying in step d) comprises using a quantitative gas-liquid chromatography method.

10. The method of claim 1, wherein said rates of absorption are used to calculate one or more coefficients of fat absorption (CFAs).

11. The method of claim 10, wherein one or more of said CFAs is used to diagnose a fat malabsorption disorder in said mammal.

12. A kit for diagnosing a pancreatic-based fat malabsorption disorder in a mammal, said kit comprising
   a) an instructional material;
   b) a digestible composition consists of a first fatty acid-containing substrate which can be absorbed from the small intestine of the mammal in the absence of pancreatic lipase hydrolysis thereof and a second fatty acid-containing substrate which cannot be absorbed from the small intestine of the mammal in the absence of pancreatic lipase hydrolysis thereof, wherein said first fatty acid-containing substrate is selected from the group consisting of pentadecanoic acid (PA) and heptadecanoin (HA) and said second fatty acid-containing substrate is selected from the group consisting of tripentadecanoic acid (TPA) and triheptadecanoin (THA); and c) a tube or vial for obtaining a sample of blood from said mammal.

13. A method as claimed in claim 1, wherein said pancreatic-based fat malabsorption disorder is pharmaceutically induced.

14. A method as claimed in claim 13, wherein said disorder is induced by administration of orlistat to said control mammal.

15. A method as claimed in claim 1, optionally further comprising assessing said mammal's stool for the levels of said free fatty acid and said triglyceride.

* * * * *

UNITED STATES PATENT AND TRADEMARK OFFICE
CERTIFICATE OF CORRECTION

PATENT NO. : 7,402,405 B2  
APPLICATION NO. : 10/162837  
DATED : July 22, 2008  
INVENTOR(S) : Virginia A. Stallings It is certified that error appears in the above-identified patent and that said Letters Patent is hereby corrected as shown below:

Title Page, Item (75), Inventor  
Please delete "Geln Mills" and insert therefor --Glen Mills--.

Signed and Sealed this

Second Day of December, 2008

JON W. DUDAS  
*Director of the United States Patent and Trademark Office*